(12) United States Patent
Glidewell

(10) Patent No.: US 11,252,551 B2
(45) Date of Patent: Feb. 15, 2022

(54) SYSTEMS AND METHODS FOR EMERGENCY PREPAREDNESS

(71) Applicant: Boomboxdr LLC, Madison, MS (US)

(72) Inventor: Donald Glidewell, Madison, MS (US)

(73) Assignee: Boomboxdr LLC, Madison, MS (US)

( * ) Notice: Subject to any disclaimer, the term of this patent is extended or adjusted under 35 U.S.C. 154(b) by 0 days.

(21) Appl. No.: 16/817,484

(22) Filed: Mar. 12, 2020

(65) Prior Publication Data

US 2020/0296565 A1 Sep. 17, 2020

Related U.S. Application Data

(60) Provisional application No. 62/818,004, filed on Mar. 13, 2019, provisional application No. 62/883,609, filed on Aug. 6, 2019, provisional application No. 62/883,610, filed on Aug. 6, 2019.

(51) Int. Cl.
| | |
|---|---|
| *H04W 4/90* | (2018.01) |
| *H04W 4/021* | (2018.01) |
| *H04W 4/33* | (2018.01) |
| *H04W 4/02* | (2018.01) |
| *G16H 40/20* | (2018.01) |
| *G16H 10/60* | (2018.01) |

(52) U.S. Cl.
CPC .............. *H04W 4/90* (2018.02); *G16H 10/60* (2018.01); *G16H 40/20* (2018.01); *H04W 4/021* (2013.01); *H04W 4/33* (2018.02)

(58) Field of Classification Search
CPC ......... H04W 4/90; H04W 4/021; H04W 4/33; H04W 4/023; G16H 40/20; G16H 10/60; G16H 40/67; G16H 10/65
See application file for complete search history.

(56) References Cited

U.S. PATENT DOCUMENTS

| | | | | |
|---|---|---|---|---|
| 11,048,891 | B1* | 6/2021 | Linn | G06K 7/10366 |
| 2005/0071198 | A1* | 3/2005 | Krupa | G16Z 99/00 705/2 |
| 2008/0021834 | A1* | 1/2008 | Holla | H04L 63/0428 705/51 |
| 2008/0319805 | A1* | 12/2008 | Burke, Jr. | G06Q 50/12 705/5 |
| 2011/0054946 | A1* | 3/2011 | Coulter | G16H 30/20 705/3 |
| 2017/0161433 | A1* | 6/2017 | Perretta | G16H 30/20 |
| 2017/0311191 | A1* | 10/2017 | Khawer | H04L 27/0006 |
| 2018/0026846 | A1* | 1/2018 | Walker | H04H 20/423 370/228 |
| 2018/0240545 | A1* | 8/2018 | Brown | G16H 40/20 |
| 2020/0066398 | A1* | 2/2020 | Kejriwal | G16H 10/60 |

* cited by examiner

*Primary Examiner* — Wesley L Kim
*Assistant Examiner* — Hung K Du
(74) *Attorney, Agent, or Firm* — Foley & Lardner LLP

(57) ABSTRACT

A mobile response unit for disaster relief, the system including a router configured to connect to one or more wireless network connections, a transmitter configured to connect one or more user devices to the one or more network connections, and a processing circuit including a processor and memory, the memory having instructions stored thereon that, when executed by the processor, cause the processing circuit to retrieve and store one or more medical records from an external computing system, and wherein the router combines the one or more wireless network connections to form a high-bandwidth bonded failover connection.

19 Claims, 15 Drawing Sheets

1410 — Receive request to transfer resident

1420 — Retrieve resident data

1430 — Push resident data to receiving facility

1440 — Update local records

FIG. 14

SYSTEMS AND METHODS FOR EMERGENCY PREPAREDNESS

CROSS-REFERENCE TO RELATED APPLICATIONS

The present application claims the benefit and priority to U.S. Provisional Patent Application No. 62/818,004, filed on Mar. 13, 2019, U.S. Provisional Patent Application No. 62/883,609, filed on Aug. 6, 2019, and U.S. Provisional Patent Application No. 62/833,610, filed on Aug. 6, 2019, the entire disclosures of each of which are incorporated by reference herein.

BACKGROUND

Long-term care ("LTC") facilities provide housing and living assistance for residents. These LTC facilities often rely on electronic records systems to track and manage the care of residents. Natural disasters may require the evacuation of LTC facility residents. LTC facilities are required to maintain patient medical records during an evacuation. However, traditional infrastructure may be unavailable during a natural disaster. Furthermore, in the event of an evacuation of the LTC facility, portable access to the electronic records systems are needed.

SUMMARY

One embodiment of the present disclosure is a mobile response unit for disaster relief, the system including a router configured to connect to one or more wireless network connections, a transmitter configured to connect one or more user devices to the one or more network connections, and a processing circuit including a processor and memory, the memory having instructions stored thereon that, when executed by the processor, cause the processing circuit to retrieve and store one or more medical records from an external computing system, and wherein the router combines the one or more wireless network connections to form a high-bandwidth bonded failover connection.

In some embodiments, the system further including at least one of a radio tuner or a radio transmitter. In some embodiments, the system further including a television tuner. In some embodiments, the system further including a battery power source. In some embodiments, the system further including a user interface configured to present the one or more medical records to a user. In some embodiments, wherein the high-bandwidth bonded failover connection is configured to provide uninterrupted network connectivity. In some embodiments, the system further configured to facilitate voice-chatting with a remote individual. In some embodiments, wherein the one or more network connections include cellular network connections. In some embodiments, wherein the processing circuit is further configured to support an application environment that facilitates importing new functionality to the mobile response unit. In some embodiments, wherein storing the one or more medical records includes storing the one or more medical records in the memory and an external database.

Another embodiment of the present disclosure is a resident displacement manager for managing transfers between a displacing facility and a receiving facility, the resident displacement manager including a processing circuit including a processor and memory, the memory having instructions stored thereon that, when executed by the processor, cause the processing circuit to receive, from one or more receiving facilities, an indication of a number of available beds, display, to the displacing facility, the number of available beds, receive, from the receiving facility, an indication of a transfer of a resident to one of the available beds, and electronically send one or more records associated with the resident to the receiving facility.

In some embodiments, wherein displaying the number of available beds includes determining a number of available beds within a threshold distance of the displacing facility. In some embodiments, wherein displaying the number of available beds includes displaying an indication of a receiving facility of the one or more receiving facilities associated with each of the available beds. In some embodiments, wherein displaying the number of available beds includes displaying characteristics associated with each of the available beds. In some embodiments, wherein the resident displacement manager facilitates editing of the one or more records and creation of new records.

Another embodiment of the present disclosure is a method of managing a patient population for a disaster, the method including soliciting, from one or more receiving facilities, an indication of a number of unoccupied beds associated with each of the one or more receiving facilities, generating, for a displacing facility, an interface including an indication of each of the unoccupied beds associated with the one or more receiving facilities, retrieving, from an external database based on a selection of the unoccupied beds, one or more records associated with a patient, and transmitting, to a receiving facility of the one or more receiving facilities associated with the selection, the one or more records.

In some embodiments, wherein the interface includes an indication of a distance associated with each of the unoccupied beds. In some embodiments, wherein the interface is displayed to a user at the displacing facility on a mobile response unit. In some embodiments, wherein the mobile response unit is configured to communicate using a high-bandwidth bonded failover connection. In some embodiments, wherein the high-bandwidth bonded failover connection combines two or more cellular network connections.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE DRAWINGS

FIG. 11A is a first section of a details pane of the displacement user interface of FIG. 5, according to an exemplary embodiment.

FIG. 11B is the second section of the details pane of FIG. 11A, according to an exemplary embodiment.

FIG. 14 is a flow diagram of a method for transferring residents using the resident displacement manager of FIG. 6, according to an exemplary embodiment.

DETAILED DESCRIPTION

According to an exemplary embodiment, a mobile system for providing access to electronic medical records is described herein.

Figure 1:
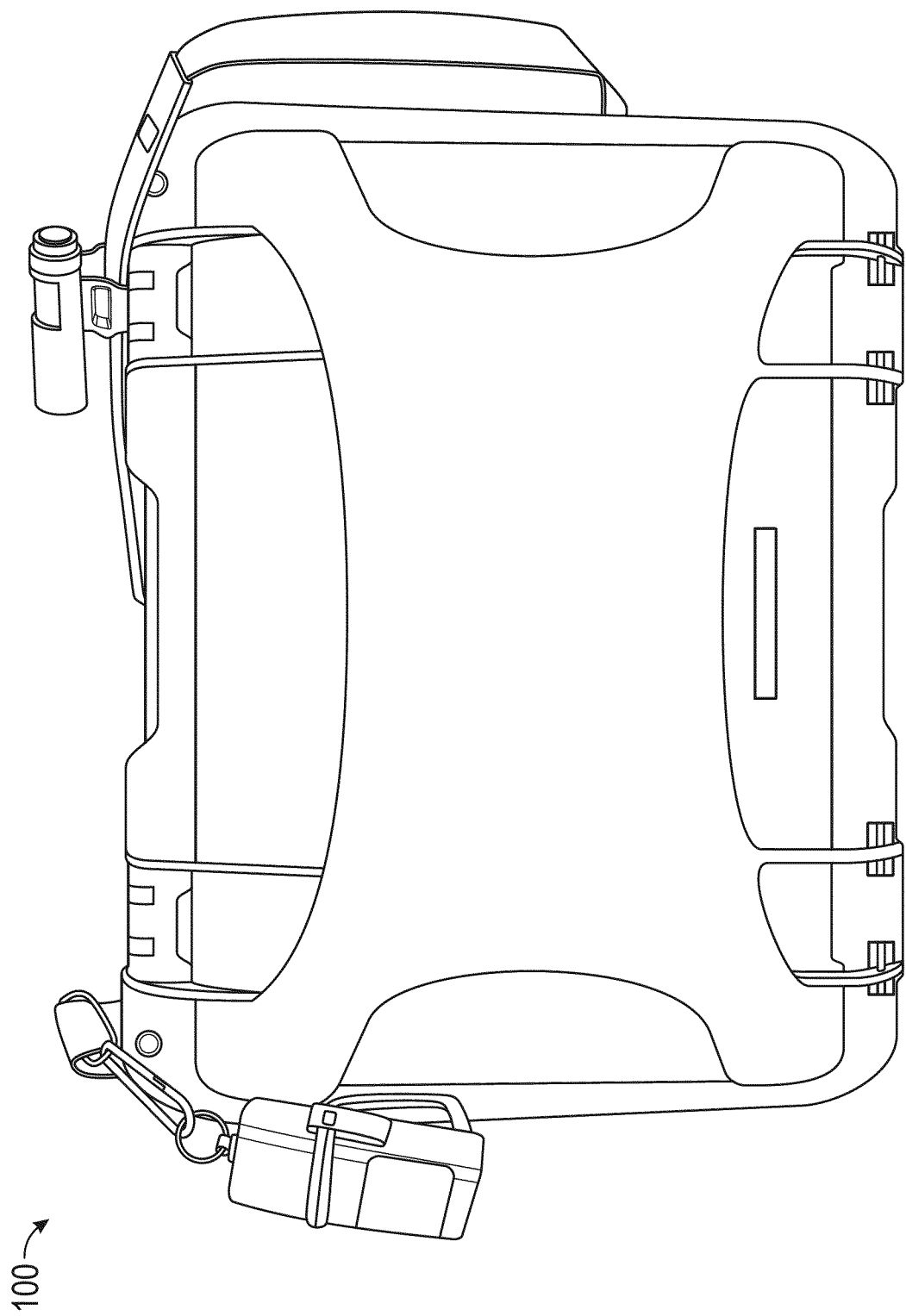
FIG. 1 is a perspective view of a mobile response unit, according to an exemplary embodiment.

FIG. 1 illustrates mobile response unit 100 for responding to emergencies and/or natural disasters. In some embodiments, mobile response unit 100 is stored at a long-term care ("LTC") facility and used in the event of emergency and/or natural disaster. In some embodiments, mobile response unit 100 is operable at a LTC facility as a stand-in for conventional systems. Additionally or alternatively, mobile response unit 100 may be portable and/or deployable from remote locations. For example, a nurse may use mobile response unit 100 to continue charting during an evacuation of a LTC facility. In other embodiments, mobile response unit 100 is used in other facilities (e.g., clinics, hospitals, daycares, schools, zoos, etc.). For example, mobile response unit 100 may be used to track the wellbeing of a number of students in a school following an active shooter event. In some embodiments, mobile response unit 100 is durable (e.g., shock-proof, drop resistant, water-proof, etc.) to avoid damage during an emergency.

Mobile response unit 100 simplifies the resident transfer process by automating many tasks associated with resident transfer and improving the transfer process. For example, LTC facility staff may traditionally call each receiving facility individually to determine a number of available beds and/or request the transfer of residents. Furthermore, medical records associated with a transferring resident may be physically printed and transferred with the transferring resident. In addition to simplifying the resident transfer process, mobile response unit 100 supports LTC facilities in complying with government regulations. For example, mobile response unit 100 may locally store medical records (e.g., retrieve and maintain an offline copy, facilitate live charting, etc.) to maintain access to the medical records even during a connectivity outage with the electronic medical record system (e.g., due to natural disaster, etc.). Additionally or alternatively, mobile response unit 100 may facilitate regulatory data compliance. For example, mobile response unit 100 may transmit electronic medical records according to an Occupational Safety and Health Administration ("OSHA") regulation and/or a Health Insurance Portability and Accountability Act ("HIPAA") regulation.

Mobile response unit 100 may provide many functions, as described in detail below. For example, mobile response unit 100 may provide a network connection (e.g., internet access, satellite connection, etc.). In some embodiments, the network connection facilitates uninterrupted access to electronic medical records ("EMR"). For example, a user may continue charting using mobile response unit 100. In some embodiments, mobile response unit 100 includes or provides emergency communications systems (e.g., HAM radio, video chat, voice over internet protocol ("VoIP"), television tuner, etc.). Additionally or alternatively, mobile response unit 100 may provide a number of emergency response functions. For example, mobile response unit 100 may provide an emergency contact list, an emergency procedure checklist, and/or an evacuation management system (e.g., resident displacement manager, etc.).

Figure 2:
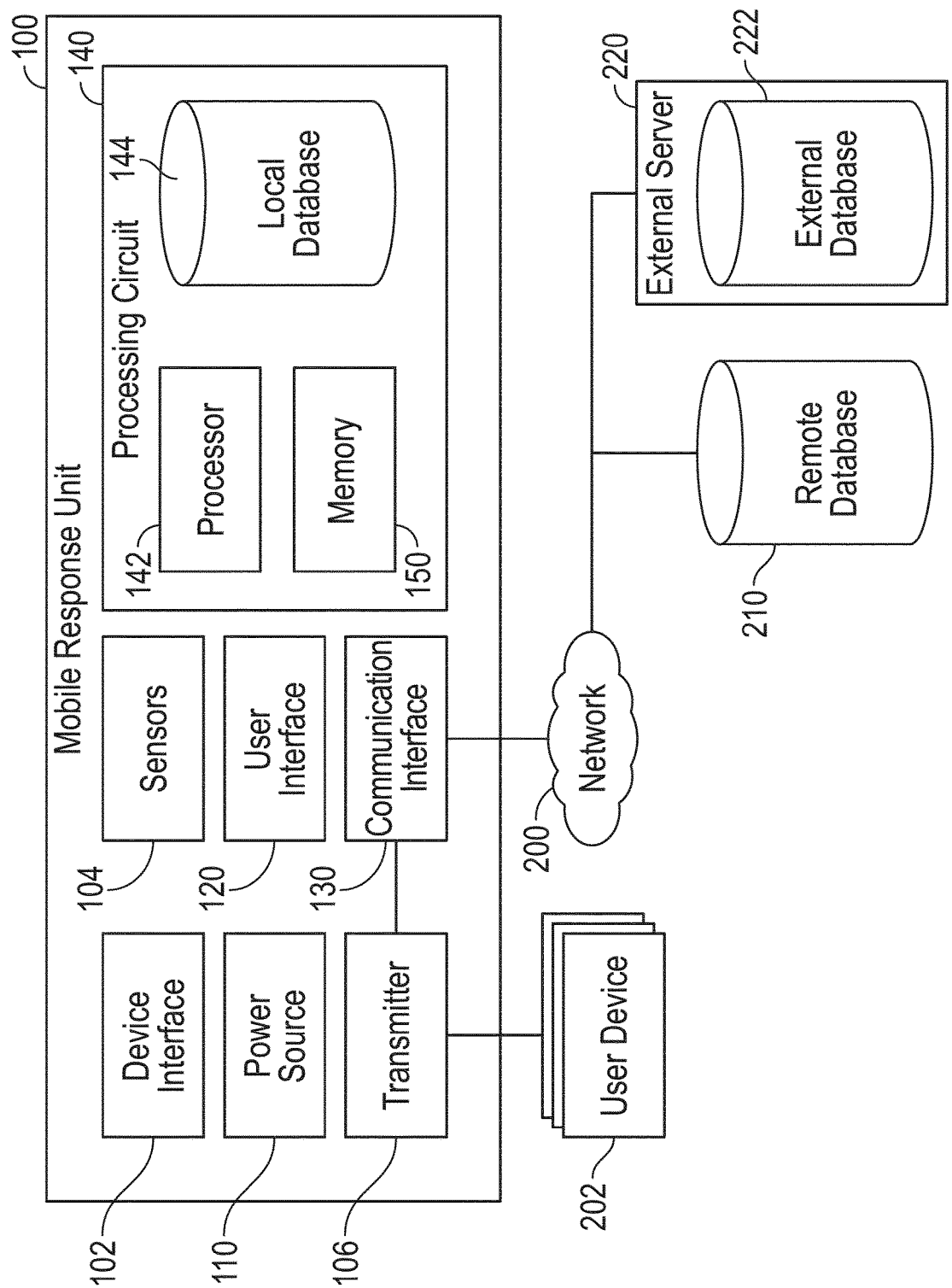
FIG. 2 is a system diagram of the mobile response unit of FIG. 1, according to an exemplary embodiment.

As shown in FIG. 2, mobile response unit 100 includes device interface 102, sensors 104, transmitter 106, power source 110, user interface 120, communication interface 130, and processing circuit 140. In some embodiments, mobile response unit 100 includes a different number, type, combination, and/or configuration of components. For example, mobile response unit 100 may include a visual signal device (e.g., a light, a flare, a balloon, etc.). In some embodiments, device interface 102 facilitates actions between mobile response unit 100 and external devices. In some embodiments, device interface 102 is or includes a number of ports (e.g., serial ports, RS-232, COM port, parallel port, audio port, VGA port, DVI port, RCA, HDMI, universal serial bus ("USB"), firewire, Ethernet (RJ45), modem (RJ14), power connectors, GPIO, etc.) and/or external devices (e.g., switches, buttons, knobs, remotes, etc.). For example, device interface 102 may include a panic alarm button configured to signal an emergency in response to engagement thereof by a user (e.g., an active shooter situation, etc.). In some embodiments, device interface 102 facilitates user interaction with or modification of processing circuit 140 and/or any other component of mobile response unit 100. For example, device interface 102 may include a subscriber identity module ("SIM") card slot for a user to insert a SIM card to interface with a router of communication interface 130. In some embodiments, device interface 102 is externally accessible to a user. For example, mobile response unit 100 may include an Ethernet port on an external surface. Additionally or alternatively, some or all of the components of device interface 102 may be located internally within mobile response unit 100 to protect them from unauthorized users and/or external elements (e.g., water, dust, etc.). In some embodiments, device interface 102 monitors (e.g., via sensors 104, etc.) the operation of one or more components of mobile response unit 100 (e.g., power source 110, transmitter 106, etc.) and transmits a message in response to an indication that the one or more components of mobile response unit 100 are malfunctioning. For example, device interface 102 may send an email to one or more individuals if transmitter 106 stops working.

According to an exemplary embodiment, sensors 104 measure one or more parameters. For example, sensors 104 may be or include temperature sensors, humidity sensors, air quality sensors, proximity sensors, light sensors, vibration sensors, and/or any other sensors. In some embodiments, mobile response unit 100 is configured to control one or more components thereof based on data from sensors 104. For example, mobile response unit 100 may increase a brightness of a display in response to a light sensor indicating that there is a significant amount of direct sunlight on the display. In some embodiments, sensors 104 include a global positioning system ("GPS") module. In some embodiments, sensors 104 are configured to detect one or more events. For example, sensors 104 may be configured to detect a gunshot.

Transmitter 106 facilitates wireless communication between mobile response unit 100 and one or more local devices. For example, mobile response unit 100, via transmitter 106, may broadcast a Wi-Fi or other wireless local area network ("WLAN") signal to provide Internet access to nearby user devices. Additionally or alternatively, transmitter 106 may transmit data to one or more cellular networks. For example, transmitter 106 may communicate with a Sprint and Verizon cellular network. In some embodiments, transmitter 106 includes a number of transmitters (e.g., five, etc.). Transmitter 106 is discussed in detail below with reference to FIG. 4.

In some embodiments, power source 110 receives and stores electrical power from a power source for future use (e.g., in a remote location where electricity is not readily available, during a power outage, etc.). In some embodiments, power source 110 includes a solar panel system, a combustion generator (e.g., a gasoline-fueled generator, etc.), a power supply (e.g., a 120 Volt ("V") AC wall charger, a 220V AC wall charger, a 240V AC wall charger, etc.), a 12V car adapter, a battery, and/or an external energy storage source (e.g., an energy tank, a battery, etc.). The stored electrical power may power mobile response unit 100 and/or a load device (e.g., a smartphone, a tablet, an E-reader, a computer, a laptop, a smartwatch, a portable and rechargeable battery pack, appliances, lights, display monitors, an electrical grid of a building, etc.) to at least one of charge and power the load device. In some embodiments, power source 110 protects against fluctuations in external power sources (e.g., electrical surges, interruptions, etc.). For example, power source 110 may be or include an uninterruptible power supply ("UPS").

User interface 120 facilitates user interaction with mobile response unit 100. In various embodiments, user interface 120 facilitates users to receive information from and provide information to mobile response unit 100. For example, user interface 120 may be or include a touch-screen display. User interface 120 is discussed in detail below with reference to FIGS. 3A-3B.

Communication interface 130 facilitates communication between mobile response unit 100 and external applications, devices, and/or systems. In some embodiments, communication interface 130 includes wired or wireless interfaces (e.g., jacks, antennas, transmitters, receivers, transceivers, wire terminals, routers, mobile broadband modems, etc.) for conducting data communication with various systems, devices, and/or networks. For example, communication interface 130 may include an Ethernet card and port for sending and receiving data via an Ethernet-based communications network and/or a Wi-Fi transceiver for communicating via a wireless communications network. In some embodiments, communication interface 130 is configured to communicate via local area networks or wide area networks (e.g., the Internet, a building WAN, etc.) and uses a variety of communications protocols (e.g., IP, etc.). In some embodiments, communication interface 130 communicates via network 200. In some embodiments, network 200 is a cellular network and/or a combination of cellular networks. For example, network 200 may be a combination of Verizon, AT&T, and Sprint networks. In various embodiments, communication interface 130 bonds multiple cellular networks together to provide a higher bandwidth signal. Additionally or alternatively, communication interface 130 may be a redundant connection. For example, communication interface 130 may be bonded and/or failover wireless internet connection. In some embodiments, communication interface 130 facilitates connecting to telemedicine support. For example, a user, via communication interface 130, may video chat with a telemedicine professional. In some embodiments, communication interface 130 facilitates sending one or more notifications (e.g., text messages, emails, automated phone calls, etc.) to notify one or more individuals. For example, communication interface 130 may automatedly call one or more family members of a resident of a LTC facility. Communication interface 130 is discussed in detail below with reference to FIG. 4.

Processing circuit 140 includes processor 142, local database 144, and memory 150. In other embodiments, local database 144 may store electronic medical records ("EMR") and/or other information. In some embodiments, local database 144 stores a local copy of external data (e.g., patient medical records, etc.) in case mobile response unit 100 loses network connection. In some embodiments, local database 144 is part of memory 150. Additionally or alternatively, local database 144 may augment memory 150.

In some embodiments, processor 142 is a general purpose or specific purpose processor, an application specific integrated circuit (ASIC), one or more field programmable gate arrays (FPGAs), a group of processing components, or other suitable processing components. In some embodiments, processor 142 is configured to execute computer code or instructions stored in memory 150 or received from other computer readable media (e.g., CDROM, network storage, a remote server, etc.).

In some embodiments, memory 150 includes one or more devices (e.g., memory units, memory devices, storage devices, etc.) for storing data and/or computer code for completing and/or facilitating the various processes described in the present disclosure. In some embodiments, memory 150 includes random access memory (RAM), read-only memory (ROM), hard drive storage, temporary storage, non-volatile memory, flash memory, optical memory, or any other suitable memory for storing software objects and/or computer instructions. In some embodiments, memory 150 includes database components, object code components, script components, or any other type of information structure for supporting the various activities and information structures described in the present disclosure. In some embodiments, memory 150 is communicably connected to processor 142 via processing circuit 140 and includes computer code for executing (e.g., by processor 142) one or more processes described herein. The functions of some of these modules is described in greater detail below with reference to FIG. 5.

In some embodiments, user device 202 is a smartphone, a tablet, a laptop computer, a desktop computer, and/or any other mobile and/or stationary computing device. For example, user device 202 may be a desktop computer used by health care professionals (e.g., nurses, doctors, etc.) at a LTC facility to record EMRs. In various embodiments, user device 202 facilitates accessing one or more features of mobile response unit 100 remotely. For example, a user using user device 202 may change configuration settings of mobile response unit 100 via an online portal.

In some embodiments, remote database 210 stores information relating to the operation of the mobile response unit 100. For example, remote database 210 may store EMRs. In some embodiments, remote database 210 stores non-critical data such as configuration settings to facilitate storing more critical data locally by mobile response unit 100, in local database 144 for example. In some embodiments, remote database 210 is a copy of an external database (e.g., external database 222, etc.). In some embodiments, remote database 210 is a "cloud" for mobile response unit 100. Additionally or alternatively, remote database 210 may back up data stored on mobile response unit 100. For example, mobile response unit 100 may periodically (e.g., daily, hourly, etc.) copy all data (e.g., memory 150, local database 144, etc.) to remote database 210. Additionally or alternatively, remote database 210 may be configured to retrieve and store data from other sources (e.g., external server 220, external database 222 etc.). For example, remote database 210 may pull EMRs from third party sources (e.g., external database 222, etc.) and store the EMRs to comply with patient privacy regulations. In some embodiments, mobile response unit 100 refreshes the data stored. For example, every three days mobile response unit 100 may retrieve new electronic medical records to replace previously stored electronic medical records.

External server 220 is an external computing system. In some embodiments, external server 220 includes a LTC facility server, an EMR server, a payroll server, and/or any other server or computing system. For example, external server 220 may be a receiving computing system of a LTC facility. In some embodiments, external server 220 includes external database 222. External database 222 may include emergency contacts, emergency procedures, EMRs, payroll data and/or any other data. For example, external database 222 may include electronic medication administration records ("eMAR"), electronic treatment authorization request records ("eTAR"), and/or activities of daily living records ("ADL"). In various embodiments, external database 222 is a number of different databases. For example, a first external database 222 may store payroll data for a LTC facility, while a second external database 222 may store EMRs relating to LTC facility residents. In some embodiments, external database 222 is separate of external server 220.

Figure 3A:
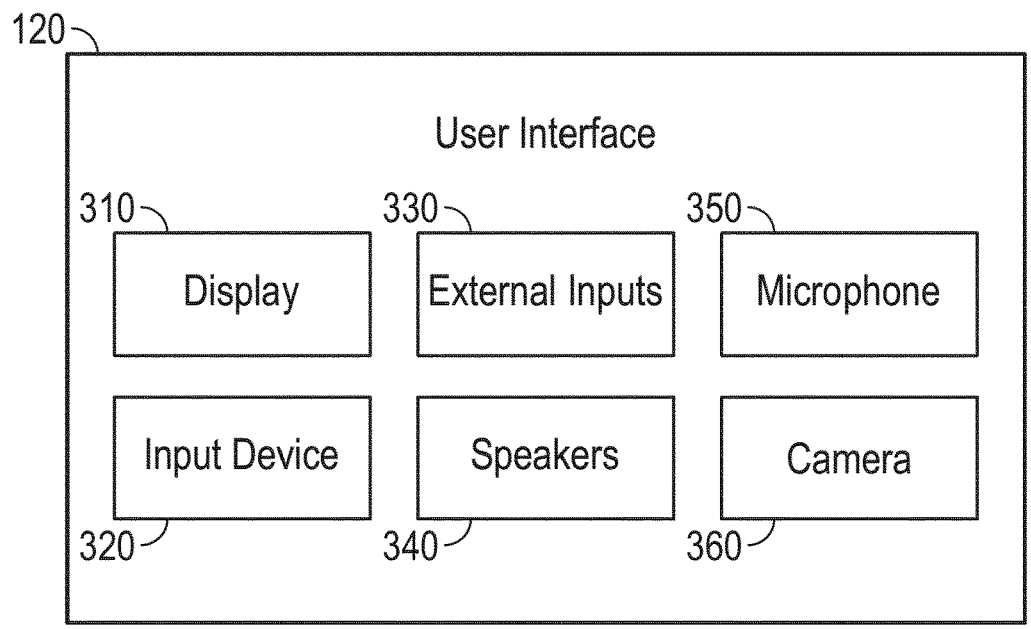
FIG. 3A is a user interface of the mobile response unit of FIG. 2, according to an exemplary embodiment.

As shown in FIG. 3A, user interface 120 includes display 310, input device 320, external inputs 330, speakers 340, microphone 350, and camera 360. In some embodiments, user interface 120 includes a different number and/or type of components. Display 310 presents visual information to a user. In some embodiments, display 310 is an electroluminescent ("ELD") display, a liquid crystal display ("LCD"), a light-emitting diode ("LED") display, an organic light-emitting diode ("OLED") display, a plasma ("PDP") display, a quantum dot ("QLED") display, an E-paper display, and/or any other display technology known in the art. In some embodiments, display 310 is a touchscreen display. Additionally or alternatively, display 310 may include a touch element. For example, display 310 may include a resistive touchscreen, a surface acoustic wave touchscreen, a capacitive touchscreen, an infrared grid touchscreen, and/or another type of touchscreen.

Input device 320 facilitates a user to provide input to mobile response unit 100. For example, input device 320 may be a keyboard, mouse, trackpad, track ball, joystick, light pen, and/or any other input device known in the art. In some embodiments, input device 320 is a single input device (e.g., a keyboard, etc.). Additionally or alternatively, input device 320 may be a combination of input devices (e.g., keyboard and mouse, etc.). External inputs 330 provide additional user inputs beyond input device 320. In various embodiments, external inputs 330 facilitate additional peripheral devices to be connected to mobile response unit 100 to expand the functionality of mobile response unit 100. In some embodiments, external inputs 330 facilitate for bulky peripheral devices to be connected to mobile response unit 100 that would otherwise not fit within the form factor of mobile response unit 100. For example, a bank of landline telephones may be connected as external inputs 330. In some embodiments, external inputs 330 include a panic alarm button. For example, a panic alarm button may facilitate a user in a remote location to send a distress signal to mobile response unit 100. In some embodiments, external inputs 330 include a handheld phone (e.g., via a RJ11 connector, etc.). In some embodiments, external inputs 330 interface with or include any of the components (e.g., Ethernet, GPIO, etc.) of device interface 102.

Microphone 350 is configured to detect and receive audio signals. In some embodiments, microphone 350 receives audio input from a user. For example, a user may interact with microphone 350 to audio-chat with an emergency response team over a VoIP connection. In some embodiments, microphone 350 provides data relating to whether a user of mobile response unit 100 is authorized. For example, mobile response unit 100 may detect an authorized user's voice signature via microphone 350. Camera 360 is used to receive visual data. In some embodiments, camera 360 allows a user to video-chat with an emergency response team. Camera 360 may capture video and/or still images.

Figure 3B:
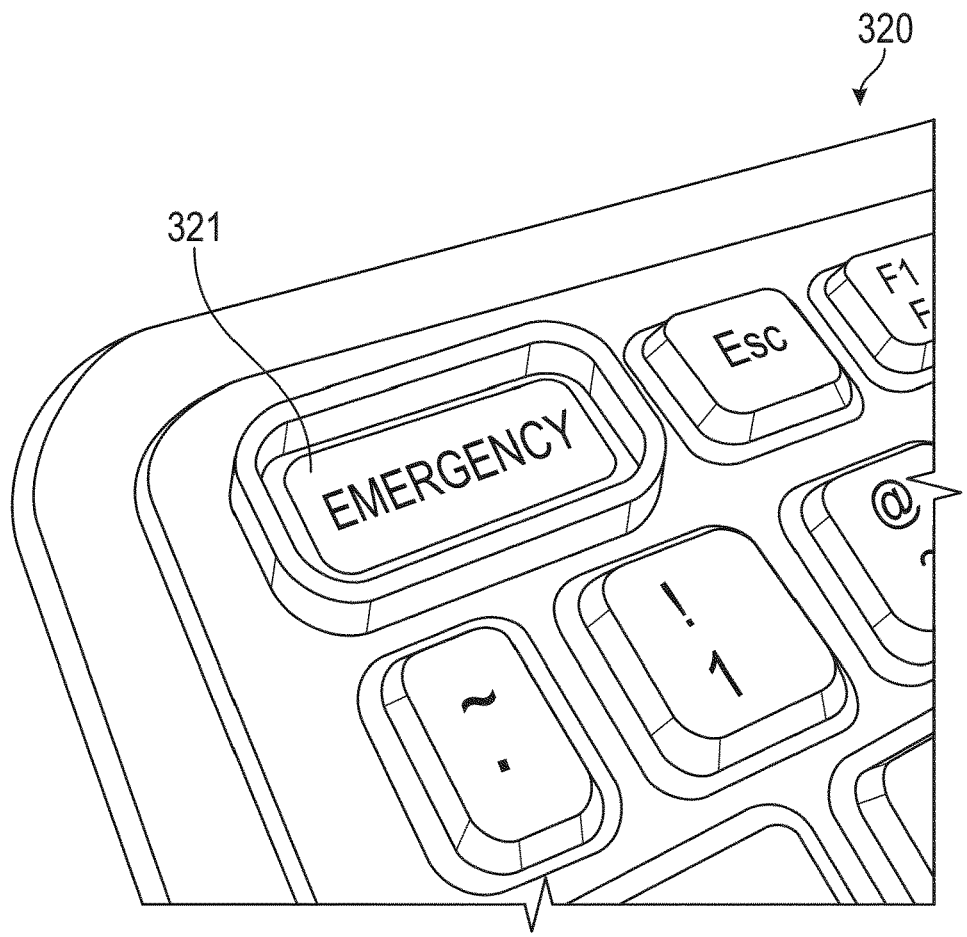
FIG. 3B is a keyboard of the user interface of FIG. 3A having an emergency key, according to an exemplary embodiment.

As shown in FIG. 3B, input device 320 includes a keyboard having an emergency key 321, according to an exemplary embodiment. For example, a user may use emergency key 321 to indicate an emergency. In some embodiments, emergency key 321 supplements and/or replaces an emergency touchscreen option on display 310. In some embodiments, use of emergency key 321 automatically contacts one or more emergency personnel. The emergency personnel may include public emergency responders (e.g., law enforcement, fire department, a "911" operator, etc.) and/or may include private response coordinators functioning as part of a first response team (e.g., staff trained to assess an emergency situation and coordinate a response, etc.). Additionally or alternatively, emergency key 321 may initiate a video and/or audio chat with one or more support individuals. For example, emergency key 321 may initiate an audio chat with an emergency dispatcher.

Figure 4:
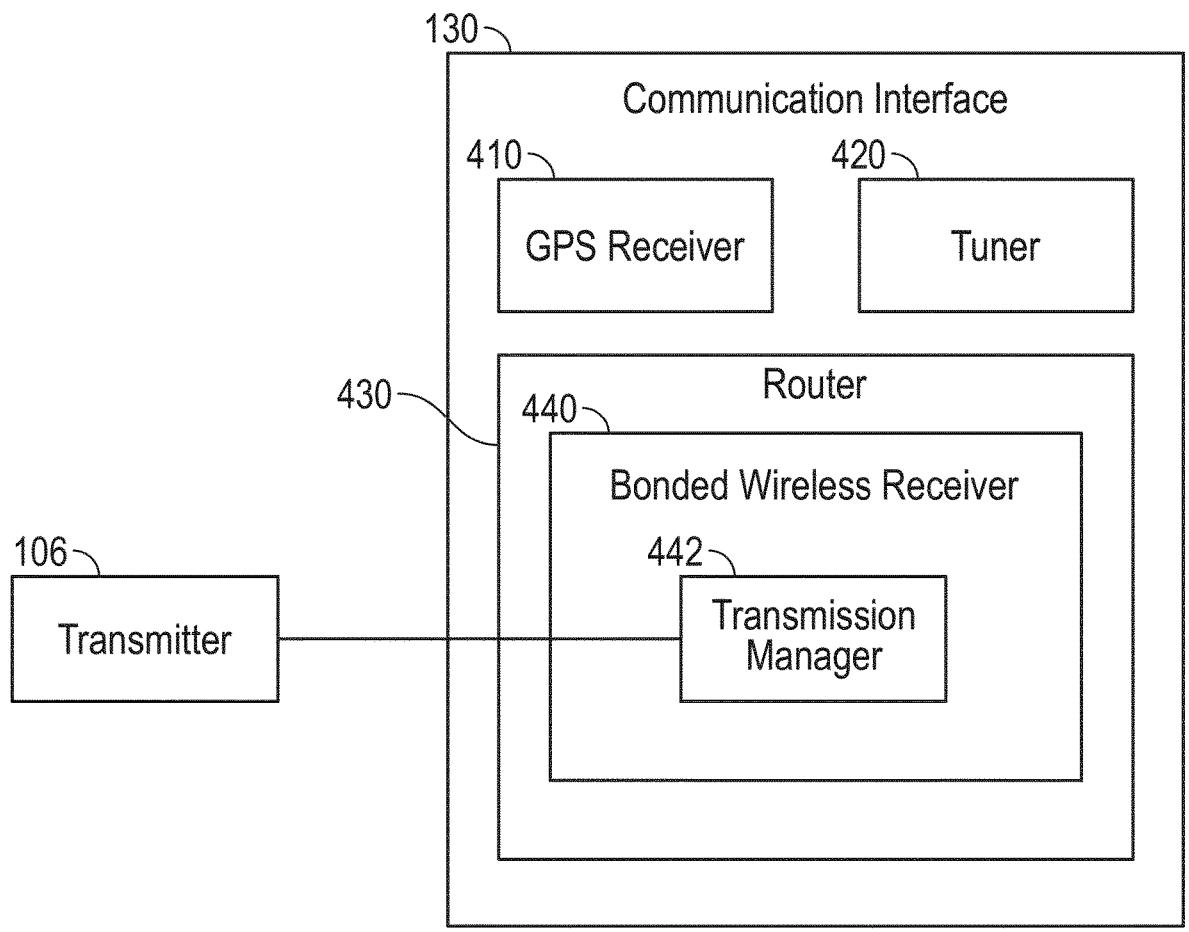
FIG. 4 is a communication interface of the mobile response unit of FIG. 2, according to an exemplary embodiment.

As shown in FIG. 4, communication interface 130 includes GPS receiver 410, tuner 420, and router 430. In other embodiments, GPS receiver 410 is configured to receive geolocation and time information from a global navigation satellite system. In some embodiments, GPS receiver 410 determines a position of mobile response unit 100 based on the received signals. For example, GPS receiver 410 may triangulate a position of mobile response unit 100 based on comparing geolocation position and time information received from several GPS satellites. Tuner 420 receives and/or decodes radio, television, and other over-the-air signals. Tuner 420 may include an antenna or other signal capture device to receive over-the-air signals. Additionally or alternatively, tuner 420 may encode and/or transmit radio, television, and other over-the-air signals. For example, tuner 420 may be configured to send and receive signals as part of a HAM radio. In some embodiments, tuner 420 receives local television broadcasts to be displayed (e.g., via display 310, etc.) by mobile response unit 100. In some embodiments, communication interface 130 includes a visual beacon. For example, communication interface 130 may facilitate connection of a helium balloon having a programmable illumination beacon. In some embodiments, the visual beacon may float above the ground as to be visible at a distance and may include an antenna and/or other transmitting and/or receiving component (e.g., GPS receiver, etc.) to facilitate communication with one or more external devices.

Router 430 directs data packets between computer networks. In some embodiments, router 430 connects to a variety of networks (e.g., LAN, WAN, the Internet, cellular networks, etc.). In some embodiments, router 430 connects one or more local devices (e.g., user device 202, etc.) to an external network (e.g., network 200, the Internet, etc.). Additionally or alternatively, router 430 may bond one or more cellular network connections together to provide a wireless network connection to mobile response unit 100. In some embodiments, router 430 transmits a Wi-Fi signal. Additionally or alternatively, router 430 may connect (e.g., via an Ethernet connection, etc.) to existing network infrastructure to provide Internet access. For example, router 430 may interface with an existing router of a LTC facility that has lost Internet access in order to restore Internet access to the LTC facility via a bonded cellular connection. In some embodiments, router 430 provides a redundant network connection (e.g., a failover Internet connection, etc.). In some embodiments, router 430 includes wireless receiver 440.

Wireless receiver 440 wirelessly communicates data over one or more network channels. In some embodiments, the network channels are cellular network channels. In some embodiments, the network channels are a mix of cellular network channels, conventional network channels, (e.g., physical transmission lines, WLAN, etc.), and/or other channels (e.g., Bluetooth, etc.). In some embodiments, wireless receiver 440 bonds (e.g., combines, transmits in parallel, etc.) multiple network channels simultaneously to provide a higher bandwidth connection than otherwise available. Additionally or alternatively, wireless receiver 440 may seamlessly transfer between network channels to provide an uninterrupted connection in the event that one or more networks lose connection.

In some embodiments, wireless receiver 440 includes and/or is coupled to one or more transmitters (e.g., transmitter 106, etc.) to transmit data to one or more cellular networks. For example, wireless receiver 440 may include a 0.6 Watt transmitter for local transmission and a 3 Watt transmitter for extended transmission. In some embodiments, the one or more transmitters transmit on one or more frequencies and/or frequency bands (e.g., 890-915 MHz, etc.). In some embodiments, a load supervisor, shown as transmission manager 442, monitors the transmission load for each transmitter and/or the router 430. For example, the number of channels may change based on current demand. For example, a Verizon network channel and a conventional network channel may be bonded to provide connection during low traffic periods, while a Verizon network channel, a Sprint network channel, and a conventional network channel may be bonded to provide a high bandwidth connection during peak traffic periods.

In various embodiments, wireless receiver 440 and/or router 430 include one or more cellular networking components (e.g., SIM cards, long-term-evolution ("LTE") adapters, etc.). In some embodiments, wireless receiver 440 includes one or more different cellular networking components, each configured to communicate on a different cellular network. For example, a LTE router may have three SIM cards, each for different cellular network carriers.

In some embodiments, transmission manager 442 is configured to allocate channels not currently in use to increase the quality of service. In some embodiments, transmission manager 442 sends packets in parallel through separate cellular, Bluetooth, and/or WLAN pathways. For example, if a Bluetooth or WLAN connection is established, transmission manager 442 may immediately route packets using the appropriate connection standard. In some embodiments, transmission manager 442 pings its environment to decide on optimal transmission medium. For example, if the signal reception is poor for a first WLAN pathway, transmission manager 442 may send some packets in parallel through both the primary WLAN pathway and a secondary communication channel (cellular, Bluetooth, and/or WLAN) to make sure some of the packets arrive at their destinations. In some embodiments, if the signal strength is adequate, transmission manager 442 prefers Bluetooth and/or WLAN pathways to minimize the number of user devices using the expensive cellular system.

Figure 5:
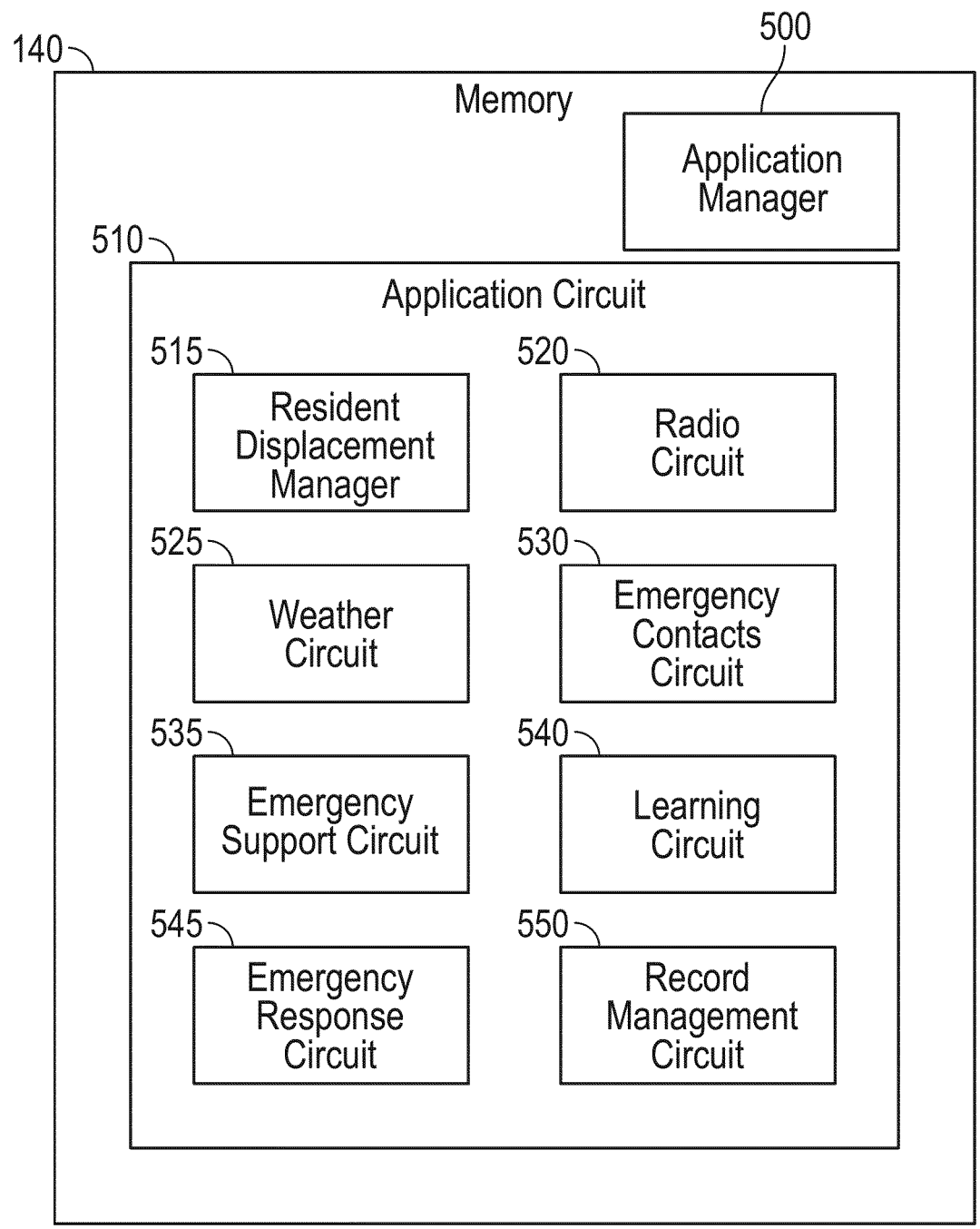
FIG. 5 is a memory of the mobile response unit of FIG. 2, according to an exemplary embodiment.

As shown in FIG. 5, memory 150 includes application manager 500 and application circuit 510, according to an exemplary embodiment. Application manager 500 manages operation of mobile response unit 100. In some embodiments, application manager 500 is configured to facilitate customization of the look and feel of the display interface of mobile response unit 100. For example, via application manager 500 a user may select from a number of applications or functionalities (e.g., functions provided by application circuit 510, etc.) to be displayed on a home screen. In some embodiments, application manager 500 is accessible via an online portal (e.g., a web application, etc.). In some embodiments, application manager 500 supports a remote desktop protocol ("RDP") connection to connect mobile response unit 100 with one or more other devices and/or services.

Application circuit 510 is embedded and/or locally executed (e.g., by mobile response unit 100, etc.) applications. For example, application circuit 510 may include embedded web applications. In some embodiments, application manager 500 facilitates a user to import new functions (e.g., components of application circuit 510) and/or select from already-loaded functions. For example, a user may embed a new function (e.g., component of application circuit 510) via a HTML link. This facilitates application manager 500 to be customizable and adapt to unforeseen needs. For example, a user could embed a payroll web application to manage payroll via mobile response unit 100. In some embodiments, functions (e.g., components) of application circuit 510 are stored locally on mobile response unit 100 (e.g., in memory 150, etc.). Additionally or alternatively, functions of application circuit 510 may be stored in remote database 210.

As shown in FIG. 5, application circuit 510 includes resident displacement circuit 515, radio circuit 520, weather circuit 525, emergency contacts circuit 530, emergency support circuit 535, learning circuit 540, emergency response circuit 545, and record management circuit 550. In other embodiments, mobile response unit 100 includes a different number, type, combination, and/or configuration of functions/circuits.

Resident displacement circuit 515 facilitates a user to track and manage a location of one or more individuals associated with a LTC facility. In various embodiments, resident displacement circuit 515 is configured to manage the relocation of LTC residents and/or staff during an emergency and/or natural disaster. For example, via resident displacement circuit 515 a user may assign LTC residents and staff to one or more different LTC evacuation facilities. For example, a LTC facility or other institution capable of providing care for LTC residents may indicate a number of available beds and a user using resident displacement circuit 515 may assign, via an interface, one or more LTC residents to the available beds. For example, a first LTC facility in Fort Lauderdale may indicate via a website a number of available beds and a second LTC facility experiencing a natural disaster in Tampa may assign its residents to the available beds via resident displacement circuit 515. Resident displacement circuit 515 is described in detail below with reference to FIGS. 6-15.

Radio circuit 520 provides radio communication functionality. In some embodiments, radio circuit 520 is a HAM radio. Additionally or alternatively, radio circuit 520 may be a web-based radio (e.g., a web-based HAM radio, etc.). For example, radio circuit 520 may launch a web-based HAM radio controller on mobile response unit 100. In some embodiments, radio circuit 520 transmits and/or receives via a radio antenna coupled to and/or included with mobile response unit 100. For example, radio circuit 520 may connect to an external radio antenna and transmit via the external radio antenna. Weather circuit 525 displays information related to weather conditions. In some embodiments, weather circuit 525 determines a location of mobile response unit 100 (e.g., via GPS receiver 410, etc.) and displays weather conditions based on the location. In some embodiments, weather circuit 525 uses one or more third party weather services. For example, weather circuit 525 may display real time satellite imagery of local weather conditions. In some embodiments, weather circuit 525 predicts the path of a weather element (e.g., a thunderstorm, a flood, a tornado, etc.) and alerts a user if they are in the predicted path. In some embodiments, weather circuit 525 is configured to detect one or more storm patterns. For example, weather circuit 525 may predict if a tornado is likely to touchdown nearby.

Emergency contacts circuit 530 includes contact information for one or more emergency contacts. In some embodiments, emergency contacts circuit 530 includes emergency contacts associated with the LTC facility. For example, emergency contacts circuit 530 may include the phone number of the manager of the LTC facility. In some embodiments, users customize the information included in emergency contacts circuit 530. In some embodiments, the information in emergency contacts circuit 530 is populated from a cloud-based database (e.g., remote database 210, etc.). In some embodiments, emergency contacts circuit 530 provides a phone number, address, email, or other information for each emergency contact. In some embodiments, emergency contacts are organized in a hierarchy. Additionally or alternatively, emergency contacts may be organized by emergency type. For example, contacts related to a natural disaster may be grouped together, and contacts related to an active shooter may be grouped together. In some embodiments, emergency contacts circuit 530 includes contact information for various government emergency lines. For example, emergency contacts circuit 530 may include the local non-emergency phone number.

In some embodiments, emergency support circuit 535 is configured to connect directly to a member of a first response team. In some embodiments, emergency support circuit 535 is coupled to (e.g., notifies devices based on data from, triggered by, etc.) emergency key 321. In some embodiments, emergency support circuit 535 facilitates a user to easily call, message, video chat, or otherwise contact emergency support personnel. For example, emergency support circuit 535 may automatically initiate a video chat with a member of a first response team. In some embodiments, emergency support circuit 535 is configured to follow an emergency procedure. For example, emergency support circuit 535 may reference a cloud-based database (e.g., external database 222, etc.) to determine an appropriate course of action. In some embodiments, emergency support circuit 535 is coupled to emergency contacts circuit 530. For example, a user may select a contact from emergency contacts circuit 530 to add to an automatic call list of emergency support circuit 535. Additionally or alternatively, emergency support circuit 535 may automatically open and initiate a call when a user selects a contact from emergency contacts circuit 530.

In some embodiments, learning circuit 540 facilitates accessing emergency preparedness ("EP") training materials. In some embodiments, EP training materials include video tutorials. In some embodiments, learning circuit 540 implements a learning plan and can track individuals' certifications and/or learning progress. For example, learning circuit 540 may require a user to complete an active shooter training and may track the user's progress through the training. Additionally or alternatively, learning circuit 540 may include manuals and/or descriptions on the functions and operation of mobile response unit 100.

Emergency response circuit 545 displays one or more emergency response plans. In some embodiments, emergency response circuit 545 includes one or more checklists and/or procedures. For example, emergency response circuit 545 may display a list of text links and/or other graphical response plans. In some embodiments, a user customizes the emergency response plans presented by emergency response circuit 545. Additionally or alternatively, emergency response circuit 545 may automatically pull the emergency response plans from a cloud-based database (e.g., external database 222, etc.). In some embodiments, the emergency response plans include static content (e.g., text documents, pictures, etc.) and/or dynamic content (e.g., web based applications, etc.).

Record management circuit 550 is configured to manage the retrieval and storage of data from external server 220 and/or external database 222. In some embodiments, record management circuit 550 is coupled to local database 144 and/or remote database 210. In some embodiments, record management circuit 550 interfaces with any of the modules and/or components of mobile response unit 100. For example, record management circuit 550 may automatically retrieve EMR data associated with residents of a LTC facility from a third party EMR provider serve and store the EMR data in local database 144 and/or remote database 210. In some embodiments, record management circuit 550 periodically (e.g., daily, hourly, etc.) backs up mobile response unit 100 to remote database 210. In various embodiments, a record management circuit 550 is user-customizable to determine what data is retrieved, stored, and/or backed up.

Speaking now generally, a resident displacement manager is described for managing the transfer of LTC facility residents and the maintenance of associated medical records. The resident displacement manager is configured to support LTC facility staff in transferring residents to other LTC facilities. The resident displacement manager enables other LTC facilities (e.g., receiving facilities, etc.) to indicate openings (e.g., available beds, etc.) and/or accept residents for transfer. LTC facility staff at the displacing facility (e.g., LTC facilities transferring residents to a receiving facility, etc.) review a list of receiving facilities and assign residents to the receiving facilities. The resident displacement manager transfers the medical records associated with the transferred resident to the receiving facility. In other embodiments, the resident displacement manager of the present application is used in other facilities (e.g., clinics, hospitals, daycares, schools, zoos, etc.). For example, the resident displacement manager may be used to track the wellbeing of a number of students in a school following an active shooter event.

The resident displacement manager of the present disclosure simplifies the resident transfer process by automating many tasks associated with resident transfer and improving the transfer process. For example, LTC facility staff may traditionally call each receiving facility individually to determine a number of available beds and/or request the transfer of residents. Furthermore, medical records associated with a transferring resident may be physically printed and transferred with the transferring resident. In addition to simplifying the resident transfer process, the resident displacement manager of the present disclosure supports LTC facilities in complying with government regulations. For example, the resident displacement manger may locally store medical records (e.g., retrieve and maintain an offline copy, facilitate live charting, etc.) to maintain access to the medical records even during a connectivity outage with the electronic medical record system (e.g., due to natural disaster, etc.). Additionally or alternatively, the resident displacement manager of the present disclosure may facilitate regulatory data compliance. For example, the resident displacement manager may transmit electronic medical records according to an Occupational Safety and Health Administration ("OSHA") regulation and/or a Health Insurance Portability and Accountability Act ("HIPAA") regulation. In some embodiments, the resident displacement manager of the present disclosure monitors the operation of one or more components of the resident displacement manager (e.g., a processing circuit, a fan, etc.) and notifies one or more individuals based on determining an anomaly in the operation. For example, a monthly report including a list specifying the operational status of each component of the resident displacement manager may be sent to one or more individuals.

Figure 6:
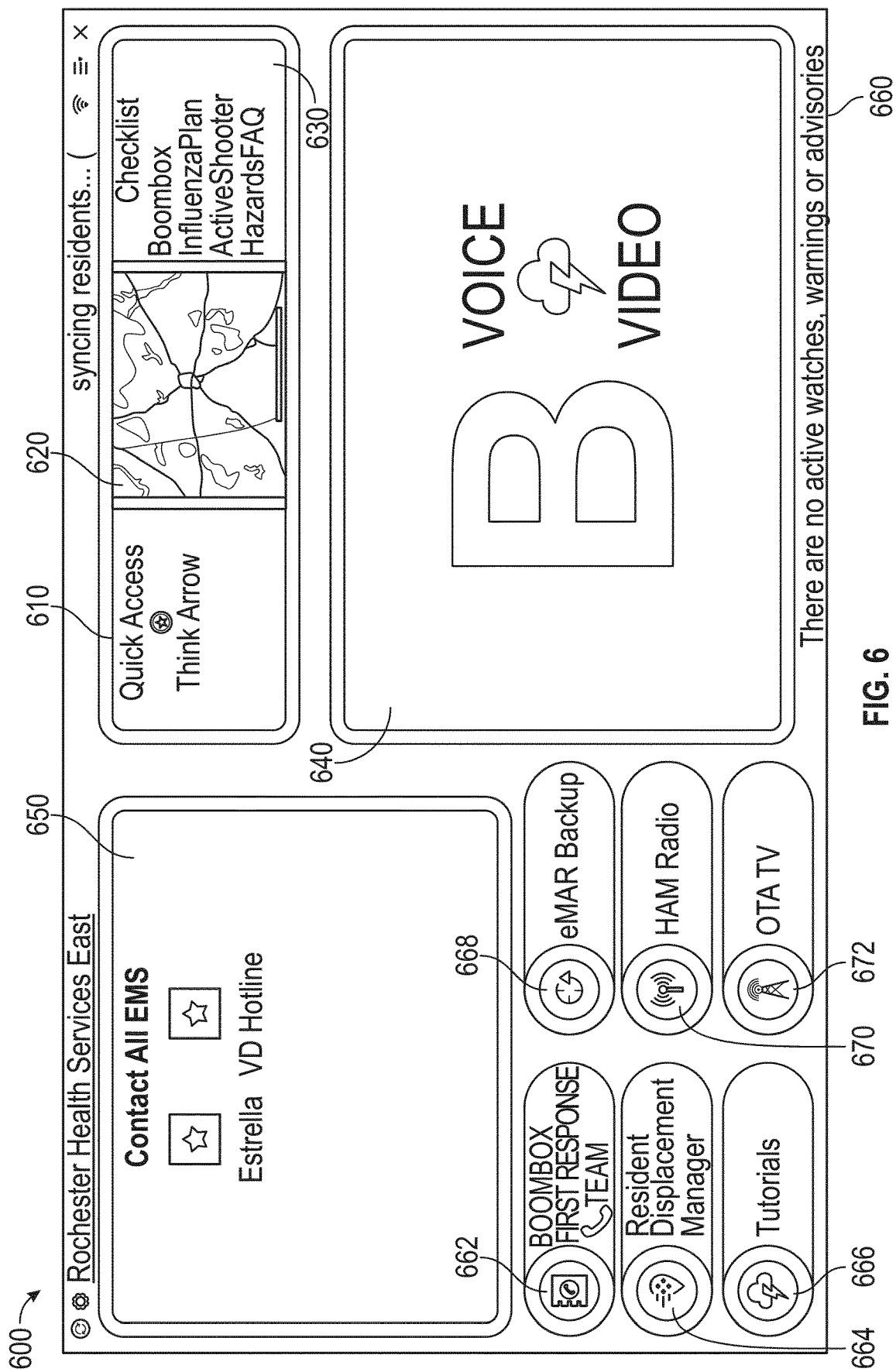
FIG. 6 is a user interface of the mobile response unit of FIG. 2, according to an exemplary embodiment.

Referring now to FIG. 6, user interface 600 of mobile response unit 100 is shown, according to an exemplary embodiment. In various embodiments, user interface 600 is displayed by display 310. In some embodiments, user interface 600 is a home screen of mobile response unit 100. In some embodiments, user interface 600 is customizable via application manager 500, as described in detail with reference to FIG. 5. User interface 600 includes resident displacement manager 664. User interface 600 includes information and functions to assist LTC staff in the event of a natural disaster or emergency. For example, user interface 600 may include emergency contacts and/or the ability to initiate a phone call with the emergency contacts. In some embodiments, user interface 600 is a user interface of an emergency device (e.g., a mobile response unit, etc.) for responding to natural disasters and/or emergencies. Additionally or alternatively, user interface 600 may be stand-alone. For example, user interface 600 may be a web application that is accessible on any computing device. In some embodiments, user interface 600 includes one or more functionalities 610-650, and a number of buttons 662-672. Functionalities 610-650 may be native applications (e.g., located on and executed by a mobile response unit, etc.). Additionally or alternatively, functionalities 610-650 may be embedded applications (e.g., widgets, etc.). In some embodiments, functionalities 610-650 are customizable (e.g., relocated, added, removed, edited, etc.) to change the appearance and/or functionality of user interface 600. Functionalities 610-650 include quick access 610, weather 620, emergency response procedure 630, emergency support 640, and/or emergency contacts 650. In some embodiments, functionalities 610-650 include a different number, type, and/or combination of functionalities 610-650. In various embodiments, functionalities 610-650 and/or buttons 662-672 correspond to components of application circuit 510. For example, resident displacement manager 664 may correspond to resident displacement circuit 515.

Buttons 662-672 provide additional functionality to functionalities 610-650. In some embodiments, buttons 662-672 represent functionalities 610-650. For example, one of buttons 662-672 may replace emergency contacts 650. In various embodiments, selection of buttons 662-672 launches one or more applications. For example, selection of resident displacement manager 664 may launch resident displacement manager 664. Buttons 662-672 are customizable as described in detail with reference to modules 610-650. Buttons 662-672 include support button 662, resident displacement manager 664, tutorials button 666, eMAR backup button 668, HAM radio button 670, and/or antenna television button 672. In some embodiments, buttons 662-672 include a different number, type, and/or combination of buttons 662-672.

Figure 7:
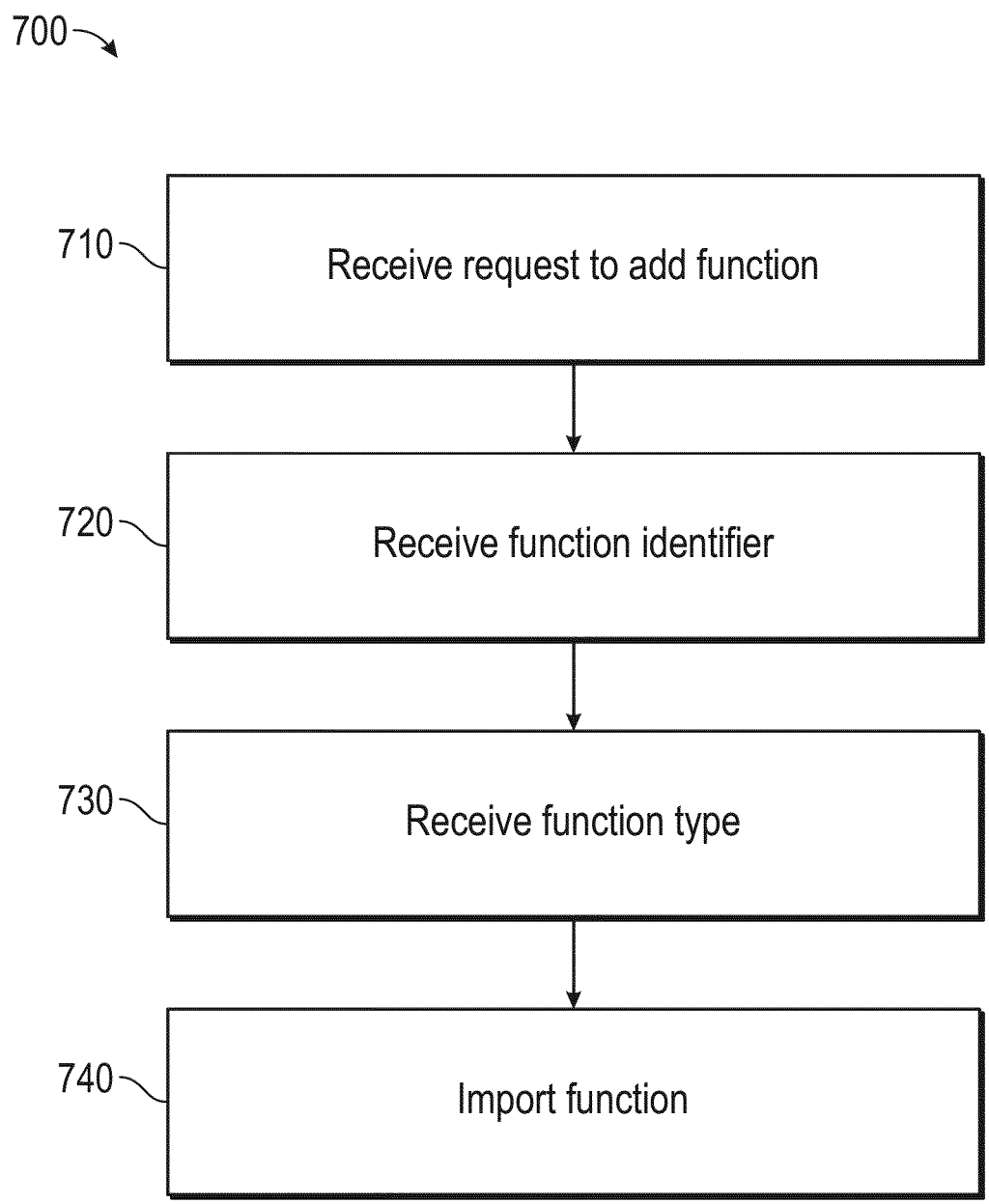
FIG. 7 is a flow diagram of a method of adding modules to the user interface of FIG. 6, according to an exemplary embodiment.

In some embodiments, as shown in FIG. 7, a method 700 of adding functions to user interface 600 is used to add new functionality to user interface 600. For example, a user may embed a web application in user interface 600 via method 700. In other embodiments, the system does not permit the user to add features or functions to, remove features or functions from, customize, or otherwise change the user interface 600. At step 710, user interface 600 receives a request to add a function (e.g., functionalities 610-650, etc.). In various embodiments, a user selects a configuration option of user interface 600 in order to initiate method 700 (i.e., step 710). At step 720, user interface receives a function identifier. In various embodiments, a user inputs a function identifier in the form of a HTML link to a web application. Additionally or alternatively, a user may provide a system path to the location in memory of the function. In some embodiments, user interface 600 is configured to detect and/or adjust to the type of identifier provided. For example, a first identifier specifying a download location for a function may download the function while a second identifier specifying a web based application may scale and embed the application.

At step 730, user interface 600 receives a function type. In some embodiments, a user indicates the function type by selecting the module type from a list. Additionally or alternatively, user interface 600 may automatically determine a function type. The function type describes the functionality of the function. For example, a first weather function may have a "news" type while a second emergency contacts function may have a "contacts" type. In various embodiments, user interface 600 adjusts method 700 based on the type of function. For example, a "news" type function may be imported as a scrolling ticker at the bottom of user interface 600 while a "contacts" type function may be imported as a function option (e.g., functionalities 610-650, etc.) on user interface 600. Additionally or alternatively, a user may customize the function prior to import. For example, the user may select a location and appearance of the function. In other embodiments, user interface 600 automatically determines a function location.

At step 740, the function is imported into user interface 600. In some embodiments, step 740 includes setup of the function. For example, specifying a location for a weather function or a list of contacts for a contacts function. In some embodiments, step 740 results in the function being displayed on user interface 600. Additionally or alternatively, step 740 may result in the function being added to a list of available functionalities that can be subsequently be used.

Resident Displacement Manager

In some embodiments, resident displacement manager 664 part of a larger emergency response solution (e.g., user interface 600, mobile response unit 100, etc.). Additionally or alternatively, resident displacement manager 664 may be a standalone system. For example, resident displacement manager 664 may be accessible as a web application on a smart phone. In various embodiments, resident displacement manager 664 includes a receiving user interface 800, as described in detail with reference to FIGS. 8-9, a displacement user interface 1000, as described in detail with reference to FIGS. 10-12, and/or one or more back-end systems, as described in detail with reference to FIGS. 13-15. In some embodiments, resident displacement manager 664 facilitates live mobile charting (e.g., reviewing, adding, modifying, etc.) of medical records.

Although elements of the present disclosure are described in terms of user interfaces (e.g., user interface 600, resident displacement manager 664, etc.), it should be understood that the systems and methods described herein may be and/or be implemented on and/or at least partially by one or more computing devices (e.g., circuits, servers, databases, microprocessors, etc.). In some embodiments, the systems and methods described herein are implemented as computer instructions (e.g., machine code, etc.) and cause one or more processors, processing circuits, and/or computing devices to carry out details described herein.

Figure 8:
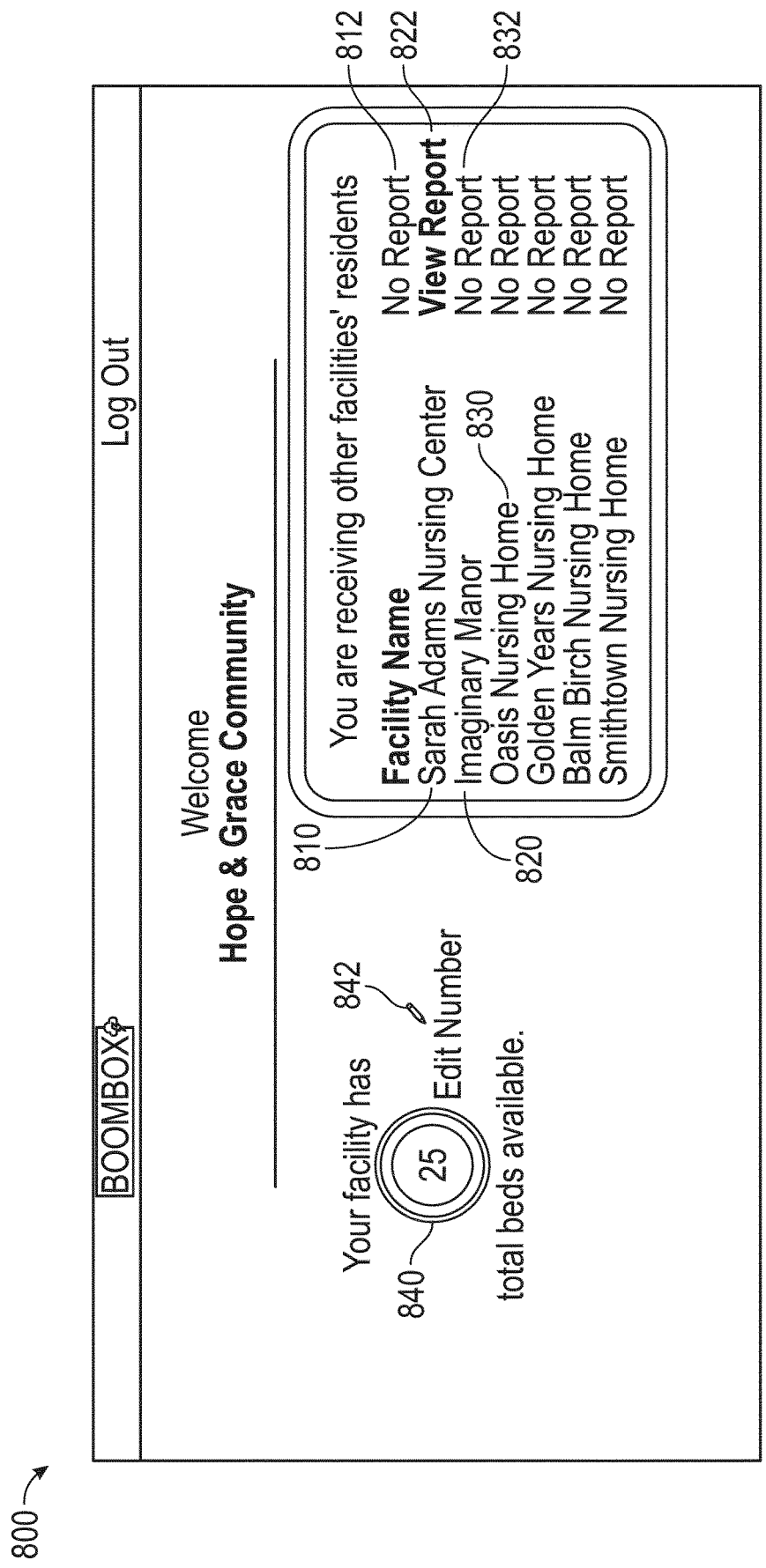
FIG. 8 is a receiving user interface of the resident displacement manager of FIG. 6, according to an exemplary embodiment.

Turning now to FIG. 8, receiving user interface 800 of the resident displacement manager is shown, according to an exemplary embodiment. In some embodiment, receiving user interface 800 is accessible from resident displacement manager 664 of user interface 600. Additionally or alternatively, receiving user interface 800 may be independent of user interface 600 (e.g., a standalone web application, etc.). For example, receiving user interface 800 may be accessible from a website and/or a mobile device application. In some embodiments, receiving user interface 800 facilitates one or more receiving facilities to indicate a number of available beds to receive residents. For example, in the event of a natural disaster (e.g., a hurricane, etc.) in Tampa, a LTC facility in Fort Lauderdale could use receiving user interface 800 to indicate to LTC facilities in Tampa how many residents they are able to receive. Furthermore, receiving user interface 800 facilitates receiving facilities to review the individual residents being transferred. For example, using receiving user interface 800, a receiving facility may view a list of which residents they are receiving. Additionally or alternatively, receiving user interface 800 may display and/or enable access to the medical records associated with the residents they are receiving. In various embodiments, resident displacement manager 664 tabulates (e.g., adds, combines, calculates, etc.) the total number of available beds by combining the number of available beds at each receiving facility. In some embodiments, resident displacement manager 664 facilitates LTC facilities to transfer LTC staff to other LTC facilities. For example, a displacing facility may transfer three residents and three health care professionals associated with the three residents to a receiving facility. A receiving facility may be able to view information about the health care professionals (e.g., name, photographs, certifications, license, specialties, etc.).

In some embodiments, the number of available beds is based on location. For example, the resident displacement manager may facilitate an indication, by displacing facilities and/or receiving facilities, of a distance threshold, and the resident displacement manager may calculate a number of available beds based on the distance threshold. As a concrete example, a first receiving facility may indicate they have 18 available beds and can receive residents from up to 25 miles away. A second receiving facility may indicate they have 12 available beds and can receive residents from up to 10 miles away. A first displacing facility may be able to transfer residents up to 15 miles away and be located 9 miles from both the first receiving facility and the second receiving facility. The first displacing facility may see that there are 30 available beds. Meanwhile, a second displacing facility may be able to transfer residents 17 miles and located 9 miles from the first receiving facility and 18 miles from the second receiving facility. The second displacing facility may see that there are 18 beds available.

Receiving user interface 800 includes a number of receiving facilities 810-830 and a number of available beds 840. Available beds 840 indicate the number of available beds the receiving facility has indicated they have available. In some embodiments, displacing facilities request an indication of a number of available beds from one or more receiving facilities. For example, a first displacing facility may have a mutual occupancy agreement with a second receiving facility. In the event of a natural disaster, the first displacing facility may request that the second receiving facility indicate a number and type (e.g., male beds, female beds, life support system equipped beds, dementia ward beds, intensive care unit beds, etc.) of available beds. In various embodiments, available beds 840 is unique to each receiving facility. Available beds 840 includes edit option 842. Edit option 842 facilitates a receiving facility to change the number of beds they indicate they have available. A method of changing the number of available beds is described in detail below with reference to FIG. 9.

Receiving facilities 810-830 lists the names and/or other information associated with each displacing facility that is transferring residents to the receiving facility. In some embodiments, receiving facilities 810-830 lists the number of residents to be received from each receiving facility. Receiving facilities 810-830 includes details 812-832. Details 812-832 provides a user with in-depth information associated with the residents to be transferred. For example, details 812-832 may include a list of the names of each resident being transferred and a link to each resident's medical records.

Figure 9:
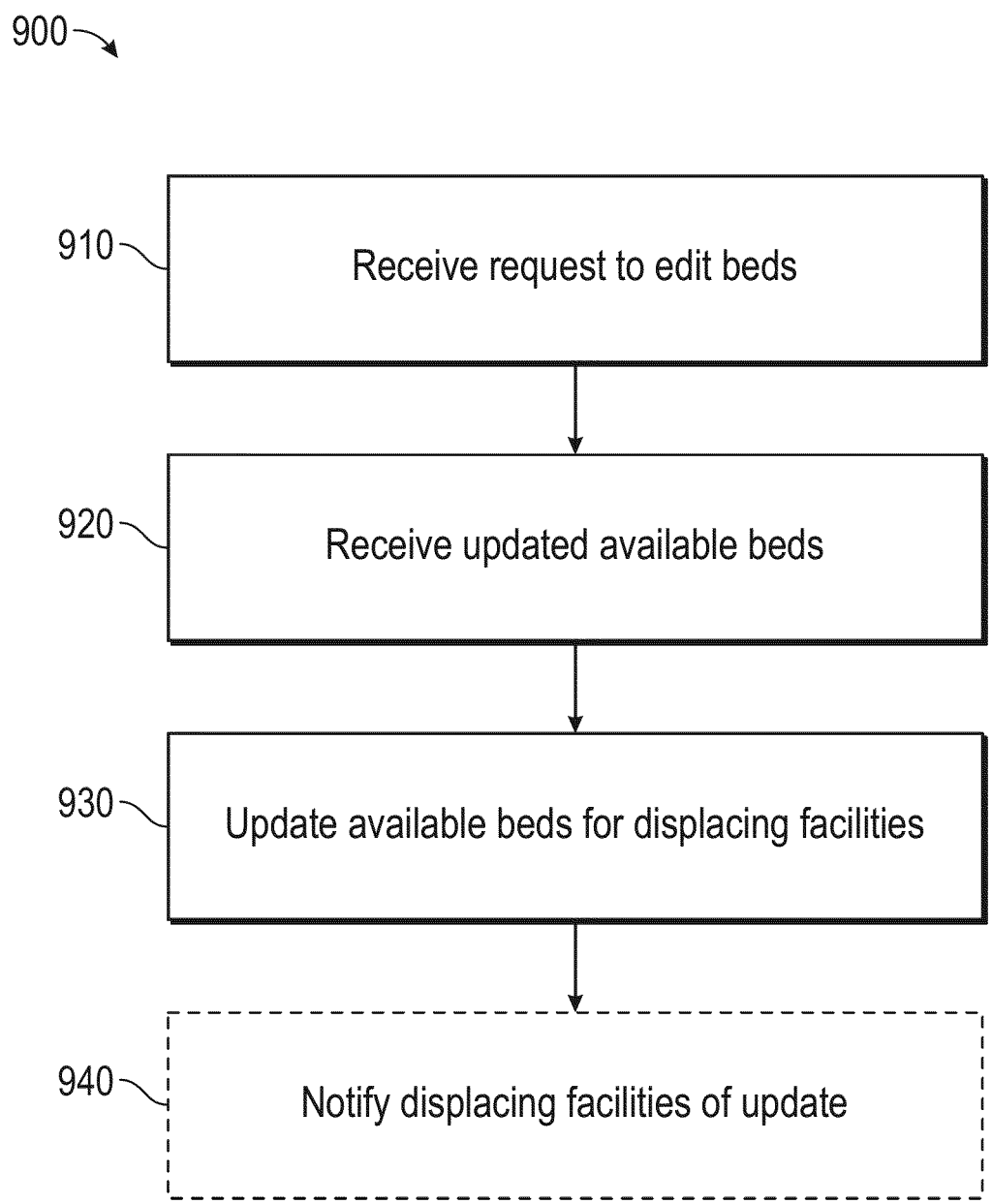
FIG. 9 is a flow diagram of a method of editing the number of available beds in the receiving user interface of FIG. 8, according to an exemplary embodiment.

As shown in FIG. 9, a method 900 is employed to edit the number of available beds. At step 910, receiving user interface 800 receives a request to edit the number of available beds (e.g., available beds 840, etc.). In various embodiments, a user selects edit option 842 to initiate method 900 (e.g., step 910). In some embodiments, step 910 includes opening a new pane and/or dialog to prompt the user and/or receive user input. For example, step 910 may include a dialog: "How many available beds do you have? _____" and a field to receive user input associated with the dialog. It should be understood that although method 900 is described in terms of receiving user interface 800 it is meant in no way to be limiting, and method 900 may additionally or alternatively be carried out, in part or in full, by resident displacement manager 664 and/or any other element described herein.

At step 920, receiving user interface 800 receives an updated number of available beds. In various embodiments, step 920 includes a user submitting an updated number of available beds to a dialog and/or input field. In some embodiments, receiving user interface 800 automatically pulls a number of available beds from a computing system associated with the receiving facility. For example, receiving user interface 800 may query the facility occupancy from a server that manages resident occupancy for the receiving facility. In some embodiments, receiving user interface 800 submits a GET request and/or any other HTTP request to a server associated with the receiving facility.

At step 930, receiving user interface 800 updates a number of available beds displayed to displacing facilities. In various embodiments, step 930 changes a number of available beds displayed to displacing facilities. In some embodiments, step 930 includes retabulating (e.g., adding, calculating, etc.) the number of available beds for each displacing facility. In some embodiments, method 900 includes step 940. At step 940, receiving user interface 800 notifies displacing facilities of the update to the number of available beds. The notification may be a push notification, an automated phone call, a text message, an email, an alert on user interface 600 and/or any other notification. In various embodiments, receiving user interface 800 determines if a displacing facility has assigned a resident to transfer to a bed that is no longer available (e.g., because a receiving facility has reduced the number of available beds, etc.) and notifies the displacing facility.

Figure 10:
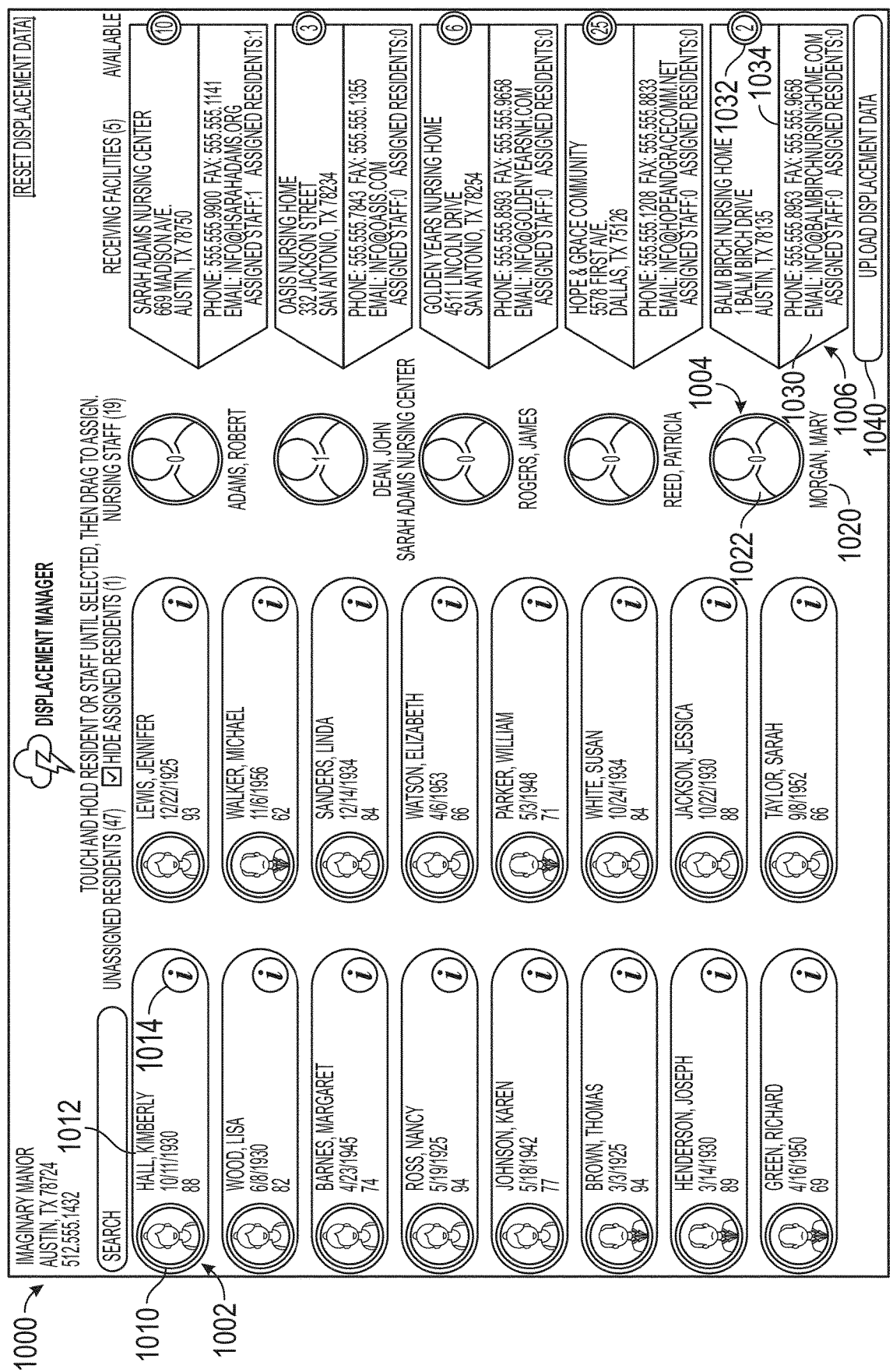
FIG. 10 is a displacement user interface of the resident displacement manager of FIG. 6, according to an exemplary embodiment.

Turning now to FIG. 10, displacement user interface 1000 for managing the transfer of LTC residents and staff is shown, according to an exemplary embodiment. In some embodiments, displacement user interface 1000 is part of user interface 600 (e.g., is or is included in resident displacement manager 664, etc.). In some embodiments, displacement user interface 1000 is part of a larger resident displacement manager (e.g., resident displacement manager 664, etc.). In various embodiments, displacement user interface 1000 is paired with receiving user interface 800. Additionally or alternatively, displacement user interface 1000 may be standalone (e.g., included in a mobile response unit separate of receiving user interface 800, etc.). For example, displacement user interface 1000 may be included in a mobile response unit for natural disaster and/or emergency relief while receiving user interface 800 may be a web based application accessible via the Internet.

Displacement user interface 1000 includes one or more resident profiles 1002, one or more staff profiles 1004, one or more receiving facilities 1006 and upload 1040. Resident profiles 1002 includes all the residents associated with the LTC facility. In some embodiments, a user manually enters resident data (e.g., by interacting with upload 1040, etc.) into displacement user interface 1000. Additionally or alternatively, displacement user interface 1000 may automatically populate at least some of resident profiles 1002, staff profiles 1004, and/or receiving facilities 1006. For example, displacement user interface 1000 may retrieve a list of residents at an LTC facility from a server associated with the LTC facility and populate resident profiles 1002 based on the list. In some embodiments, upload 1040 causes automatic population of resident and staff data. Automatic population of resident and staff data is described in more detail below with reference to FIGS. 12-13. In some embodiments, a mix of automated and manual entry is used. For example, displacement user interface 1000 may automatically populate resident profiles 1002 but allow a user to manually review and/or edit the information. In various embodiments, displacement user interface 1000 is configured to facilitate users to customize displacement user interface 1000. For example, a user may choose how many residents are displayed on each page or may choose what resident information is displayed. In some embodiments, receiving facilities 1006 are one or more LTC facilities with which the displacing facility has a mutual occupancy agreement. Additionally or alternatively, receiving facilities 1006 may include other LTC facilities (e.g., LTC facilities within a vicinity of the displacing facility, a pool of LTC facilities, etc.).

Displacement user interface 1000 facilitates a user assigning residents and staff to a receiving facility 1006. For example, a user may drag a resident profile 1002 to a receiving facility 1006 to assign the resident to the receiving facility. In various embodiments, once the resident is assigned to the receiving facility, displacement user interface 1000 may send information associated with the resident (e.g., medical records, resident profile, etc.) to the receiving facility. In some embodiments, displacement user interface 1000 sends the receiving facility a notification indicating that resident has been assigned. In various embodiments, displacement user interface 1000 facilitates assigning and/or editing one or more existing assignments. For example, a user may remove a health care professional and a resident assigned to a particular receiving facility and reassign them to a different receiving facility.

Resident profiles 1002 includes resident picture 1010, description 1012, and expand option 1014. In some embodiments, resident picture 1010 is a headshot of the resident. In various embodiments, resident picture 1010 is retrieved from medical records associated with the resident. Additionally or alternatively, resident picture 1010 may be retrieved from a server and/or database associated with the LTC facility. For example, resident picture 1010 may be retrieved from a contacts list maintained by the LTC facility. In some embodiments, displacement user interface 1000 includes the ability to take a photo of the resident. Additionally or alternatively, resident picture 1010 may be received via a website. For example, a user may upload resident picture 1010 to a website and resident picture 1010 may be imported into resident profiles 1002. In some embodiments, selection of resident picture 1010 displays an enlarged version of resident picture 1010. Additionally or alternatively, selection of resident picture 1010 may facilitate editing (e.g., change, add filters, add tags, take a new picture, etc.) of resident picture 1010. In some embodiments, description 1012 includes the name, age, date of birth, and/or allergies of the resident. In some embodiments, description 1012 includes a different number and/or type of information. For example, description 1012 may include resident aliases (e.g., nicknames, etc.).

In some embodiments, expand option 1014 facilitates viewing additional details associated with resident profile 1002. For example, expand option 1014 may display medical records associated with the resident, as described in detail below with reference to FIGS. 11A-11B. In various embodiments, a user customizes what information is displayed by expand option 1014.

Staff profile 1004 includes staff picture 1020 and assign option 1022. Similar to resident picture 1010, in some embodiments, staff picture 1020 is a headshot of the staff member. In various embodiments, staff profile 1004 includes a different number and/or type of information associated with each staff member (e.g., specialties, certifications, etc.). In some embodiments, staff picture 1020 includes any of the features described above in reference to resident picture 1010. Assign option 1022 facilitates assigning a staff member to a receiving facility (e.g., receiving facility 1006, etc.). In some embodiments, when no staff are assigned to a receiving facility 1006, assign option 1022 exists independent of staff profile 1004. In some embodiments, assign option 1022 is a button (e.g., an addition operator symbol, etc.). Additionally or alternatively, assign option 1022 may be or include staff picture 1020. Additionally or alternatively, once assigned to a receiving facility, staff profile 1004 may indicate that the staff member is assigned (e.g., by changing an appearance of staff profile 1004, etc.). In some embodiments, a user selects one or more elements of staff profile 1004 to view additional information and/or edit the information associated with the staff member.

Receiving facility 1006 includes assign button 1030, availability 1032, and facility information 1034. Assign button 1030 is configured to facilitate assigning residents (e.g., resident profile 1002, etc.) and/or staff members (e.g., staff profile 1004, etc.) to a receiving facility (e.g., receiving facility 1006, etc.). In some embodiments, assign button 1030 is a button (e.g., an addition operator symbol, etc.). Additionally or alternatively, assign button 1030 may be or include receiving facility 1006. In some embodiments, assign button 1030 opens a dialog to select one or more resident profiles 1002 and/or staff profiles 1004 for assignment. In some embodiments, assigning one or more individuals updates availability 1032. In some embodiments, availability 1032 indicates the number of available beds remaining at the receiving facility. In various embodiments, availability 1032 is linked to receiving user interface 800. For example, availability 1032 may update based on changes in the number of available beds, as described in detail above with reference to FIGS. 8-9. Facility information 1034 includes information associated with receiving facility 1006. In some embodiments, facility information 1034 includes a facility name, address, contact information, website, and/or any other information associated with the receiving facility.

Figure 11A:
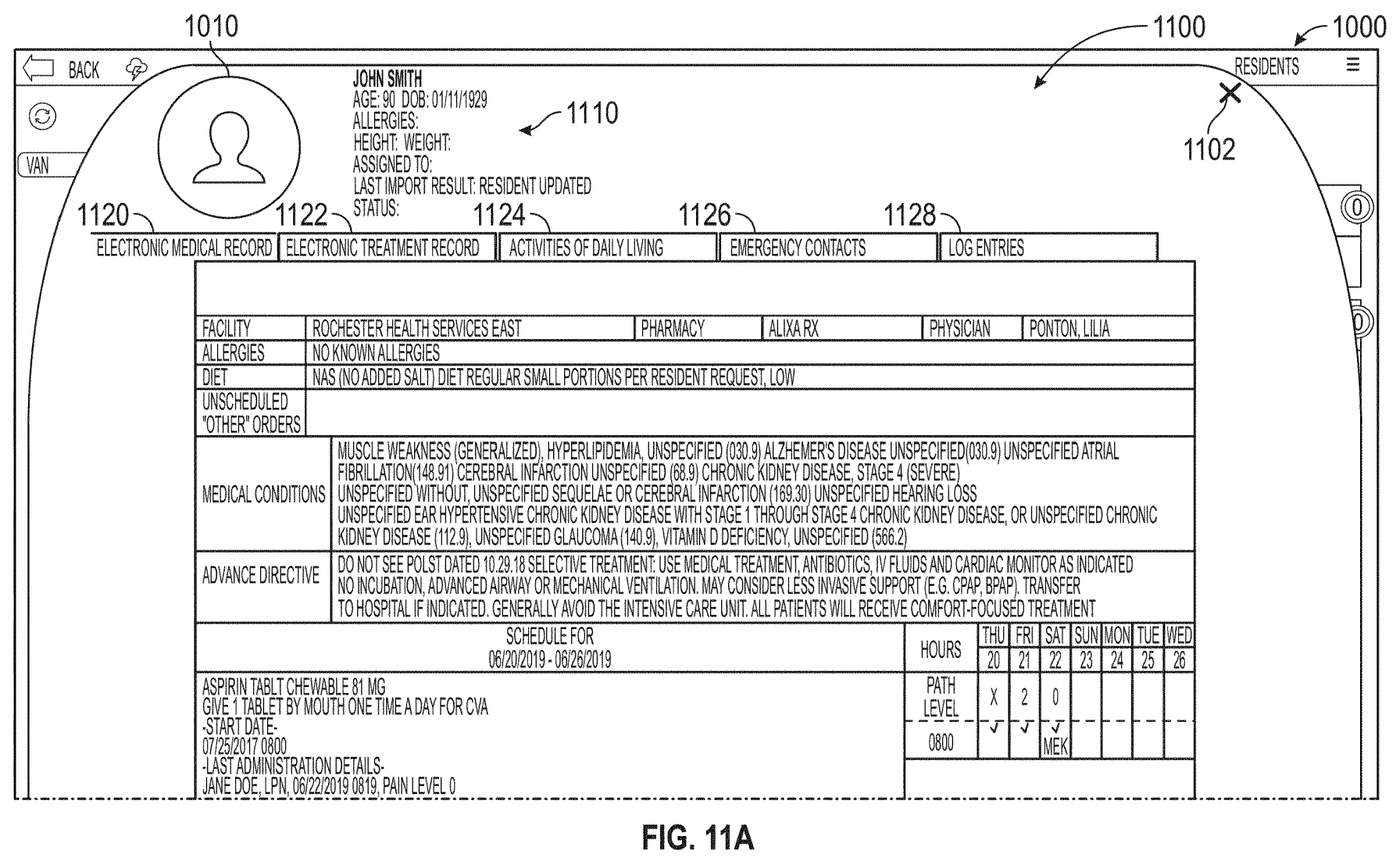
Figure 11B:
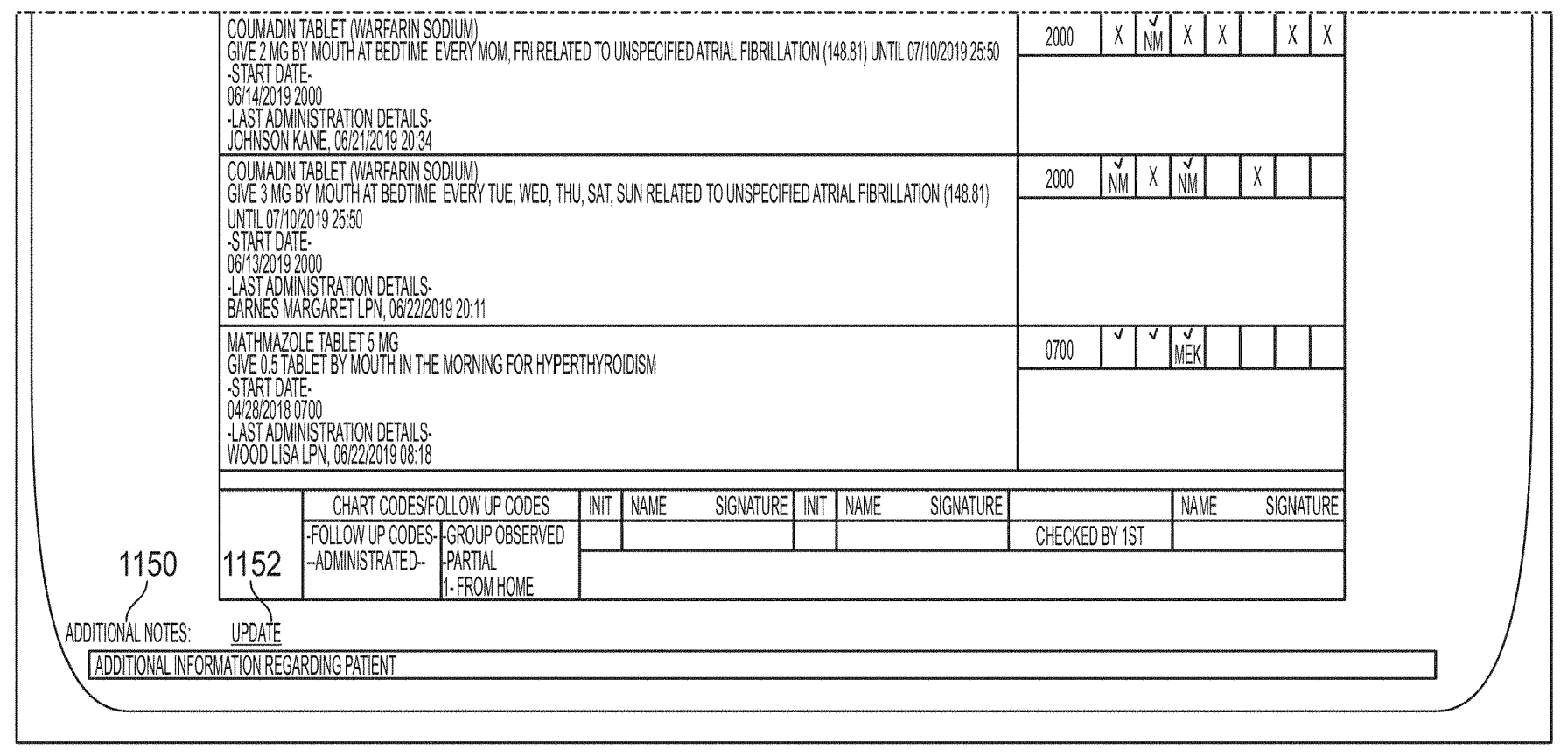

Turning now to FIGS. 11A-11B, details pane 1100 of displacement user interface 1000 is shown, according to an exemplary embodiment. In some embodiments, details pane 1100 displays in-depth information associated with a resident (e.g., resident profile 1002, etc.). In some embodiments, details pane 1100 is displayed in response to a user selecting expand option 1014. For example, details pane 1100 may display medical records associated with the resident. Details pane 1100 includes resident picture 1010, close button 1102, and one or more panes 1120-1128. Selection of close button 1102 closes details pane 1100. Additionally or alternatively, selection outside of details pane 1100 may close details pane 1100.

Panes 1120-1128 include organized information associated with a resident (e.g., resident profile 1002, etc.). In various embodiments, panes 1120-1128 are generated and/or populated based on information retrieved from a medical record associated with a resident. Panes 1120-1128 include electronic medical records 1120, electronic treatment records 1122, activities of daily living 1124, emergency contacts 1126, and log entries 1128. In some embodiments, panes 1120-1128 include a different number and/or type of panes. In various embodiments, a user may customize the appearance and contents of panes 1120-1128. In some embodiments, electronic medical records 1120 include additional notes 1150. Electronic medical records 1120 displays one or more medical records associated with the resident. In some embodiments, electronic medical records 1120 display live, up to date medical records. Additionally or alternatively, electronic medical records 1120 may display a backed up copy of the medical records.

Additional notes 1150 include update option 1152. In some embodiments, update option 1152 opens a dialog to update (e.g., edit, modify, alter, add, remove, etc.) information from one or more panes (e.g., panes 1120-1128, etc.) of details pane 1100. For example, a user may add a note about a resident's favorite activities to additional notes 1150.

Electronic treatment records 1122 includes one or more electronic treatment records. In some embodiments, electronic treatment records 1122 include a list of recent treatments a resident has received. For example, electronic treatment records 1122 may include a chart indicating when a patient has received their daily medications.

Activities of daily living 1124 includes one or more activities associated with the resident. In some embodiments, activities of daily living 1124 include exercises and/or physical therapy routines for the resident. In some embodiments, activities of daily living 1124 indicate a number of self-care routines of a resident. For example, activities of daily living 1124 may indicate that resident brushes their own teeth daily. Additionally or alternatively, activities of daily living 1124 may indicate which activities a resident needs help completing. For example, activities of daily living 1124 may indicate a resident requires help to bathe himself or herself.

Emergency contacts 1126 includes one or more emergency contacts. In some embodiments, emergency contacts 1126 includes phone numbers, email addresses, postal addresses, and/or other contact information. In some embodiments, emergency contacts 1126 includes one or more pictures and/or name pronunciations associated with the listed emergency contacts. Log entries 1128 includes one or more record and/or log entries. In some embodiments, log entries 1128 includes a history of recent updates to resident profile 1002. For example, log entries 1128 may indicate the last time the information associated with the resident was retrieved from a master electronic medical record. In some embodiments, log entries 1128 includes one or more notes taken by a health care professional. For example, log entries 1128 may include a note indicating the resident felt ill after consuming dairy.

Figure 12:
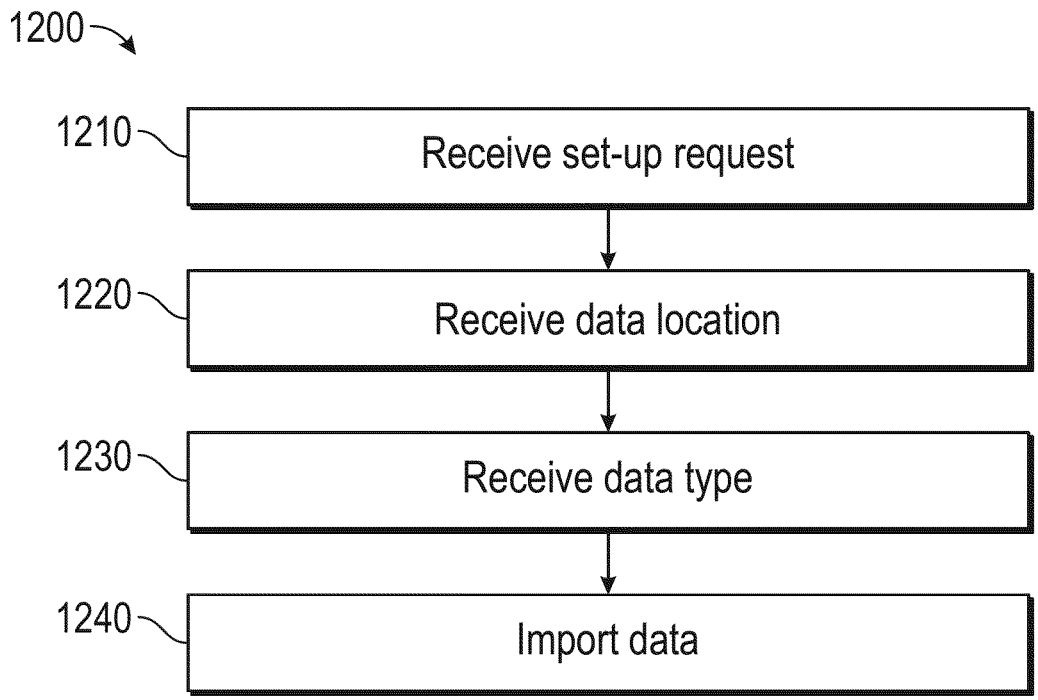
FIG. 12 is a flow diagram of a set-up method for the resident displacement manager of FIG. 6, according to an exemplary embodiment.
Figure 13:
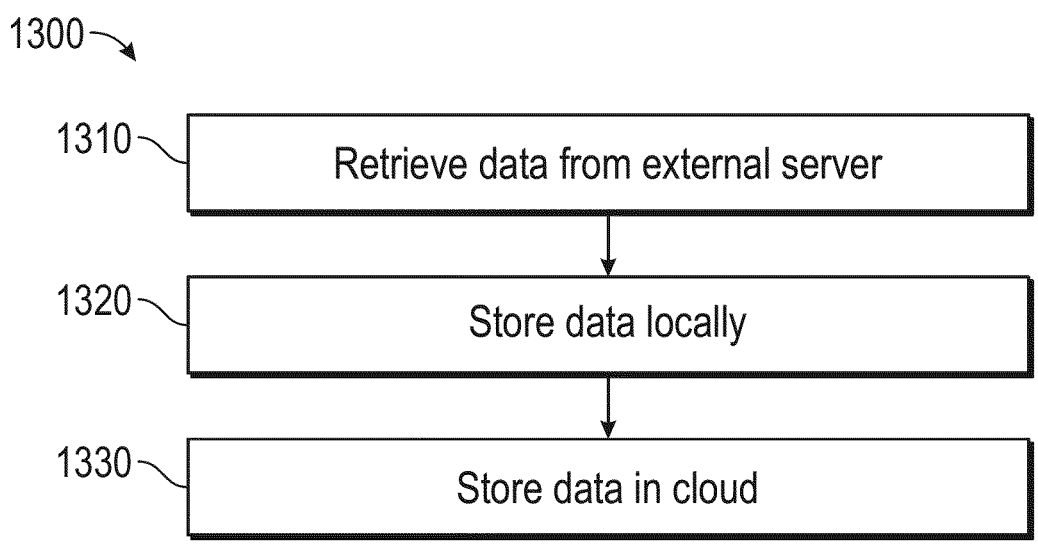
FIG. 13 is a flow diagram of a backup method for the resident displacement manager of FIG. 6, according to an exemplary embodiment.

Referring now generally to FIGS. 12-14, a number of flow diagrams are shown, according to an exemplary embodiment. In some embodiments, FIGS. 12-14 represent one or more backend systems of the resident displacement manager (e.g., resident displacement manager 664, receiving user interface 800, displacement user interface 1000, etc.) of the present disclosure. For example, the backend systems may be one or more computing devices, circuits, servers, databases, microprocessors, routines, threads, virtual machines, containers, or the like. Additionally or alternatively, one or more devices (e.g., a mobile response unit, etc.) may act in coordination with the backend systems.

As shown in FIG. 12, a method 1200 of set-up for resident displacement manager 664 is performed during a configuration (e.g., set-up, etc.) and/or installation process for resident displacement manager 664. Additionally or alternatively, method 1200 may be performed to import and/or update data. For example, a user, via method 1200, may import medical records into resident displacement manager 664 to automatically populate displacement user interface 1000. In other embodiments, resident displacement manager 664 omits method 1200. In some embodiments, method 1200 occurs automatically in response to an event (e.g., a stale data server response, etc.). In some embodiments, method 1200 is triggered by a user (e.g., via upload 1040, etc.). In various embodiments, method 1200 facilitates customizing (e.g., adding/removing modules, changing a layout, changing a look and feel, etc.) resident displacement manager 664.

At step 1210, a user interface (e.g., receiving user interface 800, displacement user interface 1000, etc.) of resident displacement manager 664 receives a set-up request. In various embodiments, a user selects a configuration menu option to perform step 1210. At step 1220, a user interface of resident displacement manager 664 receives a data location. In some embodiments, the data location is a server and/or database address (e.g., an IP address, a MAC address, etc.). Additionally or alternatively, the data location may be a file path and/or a link (e.g., a HTML link, etc.) to a file or other electronic medium having the data. In some embodiments, step 1220 includes pinging (e.g., issuing a packet internet groper ("PING") command, etc.) the location indicated by the data location to verify that it is valid.

At step 1230, a user interface of the resident displacement manager 664 receives a data type. The data type may indicate a source of the data. For example, the data type may indicate the data location is a server or a cloud based document. Additionally or alternatively, the data type may indicate a category of data. For example, the data type may indicate the data at the data location is medical records. In some embodiments, method 1200 handles the data differently depending on the data type. For example, a first "contacts" data type may be parsed to extract contacts for a LTC facility contacts list, while a second "medical records" data type may be linked to resident profiles in displacement user interface 1000.

At step 1240, a user interface of the resident displacement manager 664 imports the data specified by the data location. In various embodiments, step 1240 varies based on the data type of the data being imported. For example, "medical records" data may be stored locally on a device (e.g., a mobile response unit, etc.) and also redundantly uploaded to a cloud server, while "contacts" data may be only saved locally. In some embodiments, importing the data includes populating one or more user interfaces (e.g., receiving user interface 800, displacement user interface 1000, etc.). For example, step 1240 may include generating a number of resident profiles 1002 based on resident data from a LTC facility. In some embodiments, step 1240 modifies already existing data and/or combines multiple data sources. For example, step 1240 may include generating a number of resident profiles 1002 based on a combination of resident data and medical records (e.g., EMR, etc.) data. In various embodiments, method 1200 is used to import data of any kind. For example, method 1200 may import contacts into a contacts module (e.g., emergency contacts 650, etc.) of user interface 600.

As shown in FIG. 13, a method 1300 of backup is performed automatically (e.g., on a schedule, in response to a stale data server response, etc.) to refresh data and/or maintain up to date records. Although method 1300 is described in terms of backing up data from an external server, it should be understood that method 1300 also applies to backing up local data. In some embodiments, method 1300 is data specific. For example, medical records may be backed up hourly while contacts may be backed up monthly. In some embodiments, method 1300 is performed at least partially in associated with method 1200. For example, method 1300 may be understood to be part of step 1240 of method 1200.

At step 1310, data is retrieved from an external server. In some embodiments, the external server is a third party server. For example, the external server may be an electronic medical record provider server. In some embodiments, the external server can be a different data source (e.g., a database, a spreadsheet, etc.). In some embodiments, step 1310 includes a GET request and/or any HTTP request to the external server. In some embodiments, the method of retrieval depends on the data source (e.g., external server, etc.) type. For example, first data may be retrieved from a first server using a GET request while second data from a second server may be retrieved via a publish/subscribe model. Accordingly, in some embodiments, a data push initiates method 1300 instead of an active retrieval (e.g., a GET request, etc.). In some embodiments, step 1310 includes parsing the retrieved data. For example, the retrieved data may be an unordered list of contacts, and step 1310 may include alphabetizing and/or categorizing the list. In some embodiments, step 1310 includes comparing the data at the external server to existing data to determine what data has changed. For example, step 1310 may include only retrieving new and/or changed data.

At step 1320, the data is stored locally. In various embodiments, step 1320 includes storing the data in memory. In some embodiments, step 1320 is omitted and/or the data is only stored in the cloud (step 1330). Additionally or alternatively, step 1320 may include populating one or more user interfaces (e.g., resident displacement manager 664, receiving user interface 800, displacement user interface 1000, etc.) with the data. For example, step 1320 may include populating resident profiles 1002. In some embodiments, step 1320 includes notifying a user of the update. In some embodiments, step 1320 includes an indication of what data has changed and/or is new. For example, an appearance of newly imported resident profiles 1002 may be changed.

At step 1330, the data is stored in the cloud. In various embodiments, step 1330 includes storing the data in memory of one or more remotely hosted computing devices, circuits, servers, databases, a combination thereof, or the like. In some embodiments, the cloud is a computing device maintained by the LTC facility. In some embodiments, step 1330 includes a RESTful API (e.g., PUT request, POST request, etc.) to interact with the cloud. Additionally or alternatively, step 1330 may include a publish/subscribe model. In some embodiments, step 1330 may include writing to an audit log to document backup of the data.

Turning now to FIG. 14, a flow diagram of method 1400 for transferring residents is shown, according to an exemplary embodiment. In some embodiments, method 1400 is performed in response to a user assigning a resident to a receiving facility, as described in detail above with reference to FIGS. 10-11B. At step 1410, a request is received to transfer a resident. In some embodiments, step 1410 includes a determination of priority (e.g., time, location, need, etc.). In some embodiments, the priority is user customizable. For example, a user may create a priority rule to reflect a term included in a mutual occupancy agreement between a displacing facility and a receiving facility. For further example, a first request for transfer from a first displacing facility located next to a severe weather event may have priority over a second request for transfer from a second displacing facility located remotely of a severe weather event. In various embodiments, the request includes information associated with the resident and the transfer (e.g., a resident ID, resident medical records, a link to resident information, an IP address of a server associated with the receiving facility, etc.).

At step 1420, resident data is retrieved. In some embodiments, step 1420 includes retrieving (e.g., downloading, acquiring a link to, etc.) resident data from a server or other location. In some embodiments, resident data is stored locally (e.g., on a mobile response unit, etc.) and is packaged for distribution. Additionally or alternatively, step 1420 may include any of the data retrieval steps described above in reference to FIGS. 12-13. In some embodiments, step 1402 includes generating and/or obtaining a pointer to the data location (e.g., an IP address of the server, etc.). In some embodiments, one or more authentication methods (e.g., passwords, keys, etc.) are included in the pointer to allow access to the data.

At step 1430, the data is pushed to the receiving facility. In some embodiments, pushing the data to the receiving facility includes sending the data to a server associated with the receiving facility. In some embodiments, step 1430 includes notifying a user associated with the receiving facility of the data. In some embodiments, step 1430 includes sending an email with the data to an email address associated with the receiving facility. Additionally or alternatively, step 1430 may include providing the receiving facility access to the data through a user interface (e.g., receiving user interface 800, etc.). In some embodiments, the data is provided to the receiving facility by sending a pointer to the data to the receiving facility. In some embodiments, step 1430 includes a RESTful API (e.g., PUT request, POST request, etc.) to interact with the receiving facility.

At step 1440, local records are updated. In some embodiments, updating local records includes updating one or more records associated with a displacing facility (e.g., a resident management server of a displacing facility, etc.). In some embodiments, step 1440 includes writing to an audit record to indicate transfer of the residents. Additionally or alternatively, device (e.g., a mobile response unit, etc.) memory may be updated to reflect the change. In some embodiments, step 1440 includes triggering a printer to print a transfer receipt. Additionally or alternatively, step 1440 may include sending one or more notifications (e.g., text messages, emails, automated phone calls, etc.) to notify one or more individuals of the transfer. For example, step 1440 may include an automated call to one or more family members of the transferred resident. Additionally or alternatively, step 1440 may include updating one or more user interfaces (e.g., resident displacement manager 664, receiving user interface 800, displacement user interface 1000, etc.). For example, availability 1032 may be updated.

Figure 15:
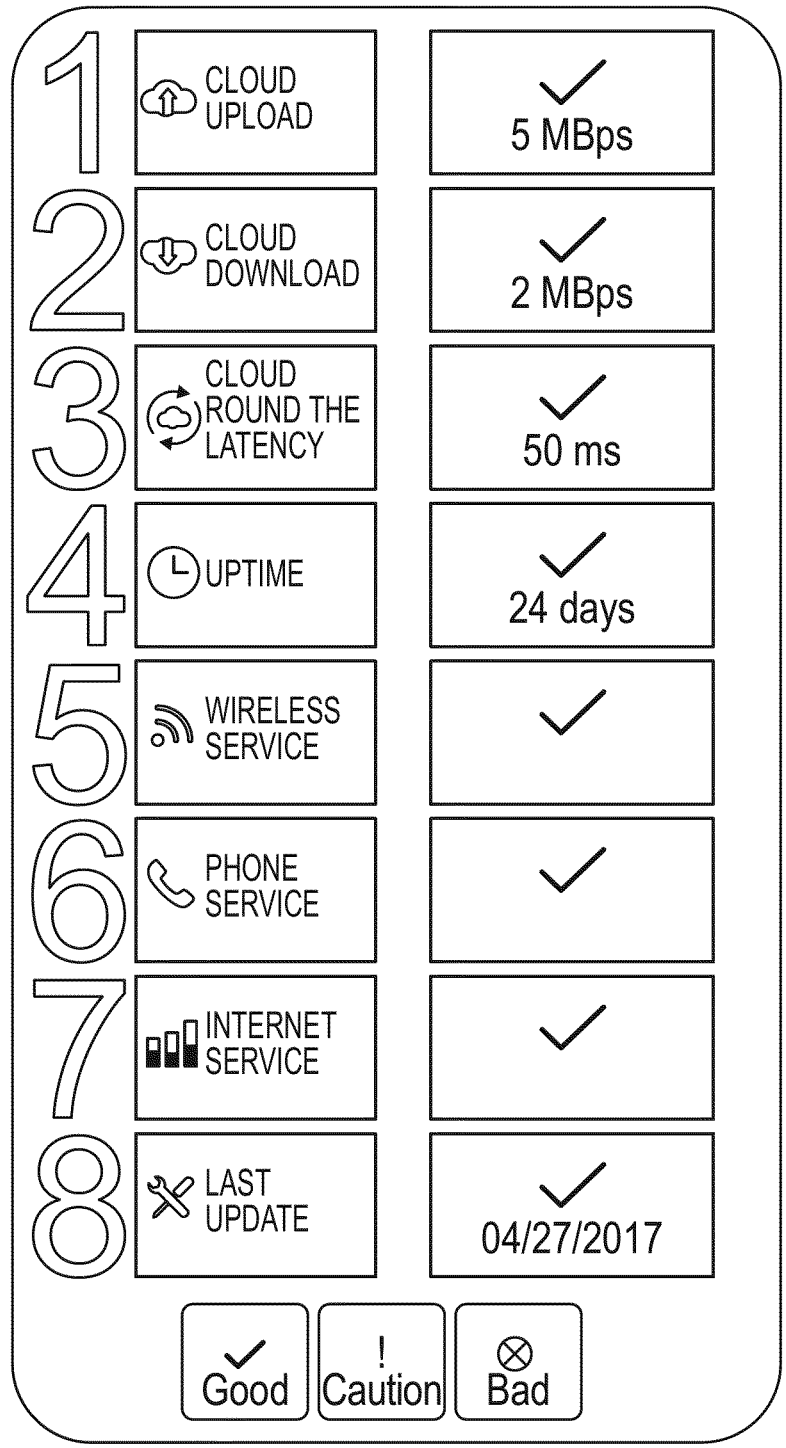
FIG. 15 is an illustration of a graphical user interface usable within the resident displacement manager of FIG. 6, according to an exemplary embodiment.

Referring now to FIG. 15, an illustrative GUI that may be used within a system for emergency preparedness (e.g., mobile response unit 100, resident displacement manager 664, etc.) is shown, according to some embodiments of the present disclosure. In some embodiments, the system may monitor, on a continuous or near-continuous basis, all facility devices (e.g., user devices 202, etc.) within the system. The illustrative GUI 1500 may provide a health check report for a particular facility device. GUI 1500 may be accessible by admins and/or members of the first response team (e.g., using respective admin devices and/or user devices 202). In some embodiments, GUI 1500 may correspond to a health check report that is sent to a facility on a periodic basis (e.g., monthly). The illustrative GUI 1500 may include several facility-related metrics, such as the status of the facility's phone and wireless service, patch information, upload time, and information regarding any outages at the facility.

The embodiments described herein have been described with reference to drawings. The drawings illustrate certain details of specific embodiments that implement the systems, methods and programs described herein. However, describing the embodiments with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As used herein, the term "medical record" may include information relating to the care of one or more individuals. Medical records may include physical records (e.g., paper documents, receipts, etc.) and/or electronic records (e.g., electronic medical records ("EMR"), administration records ("eMAR"), electronic treatment authorization request records ("eTAR"), activities of daily living records ("ADL"), etc.). Medical records may include informal records (e.g., physician recommendations, etc.) and/or formal records (e.g., post-operative reports, prescriptions, etc.).

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits ("IC"), discrete circuits, system on a chip ("SOC") circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on.

The "circuit" may also include one or more processors communicatively coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits ("ASICs"), field programmable gate arrays ("FPGAs"), digital signal processors ("DSPs"), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud-based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations.

An exemplary system for implementing the overall system or portions of the embodiments might include a computing system in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), a distributed ledger (e.g., a blockchain), etc. In some embodiments, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data that cause a general purpose computer, a special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example embodiments described herein.

It should be understood that a "network interface," as used herein, includes any of a cellular transceiver (e.g., Code Division Multiple Access ("CDMA"), Global System for Mobile Communications ("GSM"), Long-Term Evolution ("LTE"), etc.), a wireless network transceiver (e.g., 802.11X, ZigBee, or Bluetooth), an external network device (e.g., computer port, network interface card ("NIC"), network socket, port), or a combination thereof (e.g., both a cellular transceiver and a Bluetooth transceiver). In some arrangements, a network interface includes hardware and machine-readable media sufficient to support communication over multiple channels of data communication. Further, in some arrangements, the network interface includes cryptography capabilities to establish a secure, or relatively secure, communication session between one or more computing devices. In this regard, personal information about clients, medical records, financial data, and other types of data is encrypted and transmitted to prevent, or substantially prevent, the threat of hacking.

It should also be noted that the term "input devices" or "input components," as described herein, may include any type of input device including, but not limited to, a keyboard, a keypad, a mouse, joystick or other input devices performing a similar function. Comparatively, the term "output device" or "output component," as described herein, may include any type of output device including, but not limited to, a computer monitor, printer, facsimile machine, or other output devices performing a similar function.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions and arrangement of the embodiments without departing from the scope of the present disclosure as expressed in the appended claims.

What is claimed is:

1. A mobile response unit for disaster relief, the mobile response unit comprising:
    a router configured to connect to one or more wireless network connections;
    a transmitter configured to connect one or more user devices to the one or more network connections; and
    a processing circuit including a processor and memory, the memory having instructions stored thereon that, when executed by the processor, cause the processing circuit to:
        retrieve and store one or more medical records from an external computing system; and
        transmit, to a computing system, an indication of a transfer of (i) a resident and (ii) a caretaker associated with the resident from a displacing facility to a receiving facility, wherein the caretaker includes a healthcare professional; and
    wherein the router combines the one or more wireless network connections to form a high-bandwidth bonded failover connection.

2. The mobile response unit of claim 1, further including at least one of a radio tuner or a radio transmitter.

3. The mobile response unit of claim 1, further including a television tuner.

4. The mobile response unit of claim 1, further including a battery power source.

5. The mobile response unit of claim 1, further including a user interface configured to present the one or more medical records to a user.

6. The mobile response unit of claim 1, wherein the high-bandwidth bonded failover connection is configured to provide uninterrupted network connectivity.

7. The mobile response unit of claim 1, further configured to facilitate voice-chatting with a remote individual.

8. The mobile response unit of claim 1, wherein the one or more network connections include cellular network connections.

9. The mobile response unit of claim 1, wherein the processing circuit is further configured to support an application environment that facilitates importing new functionality to the mobile response unit.

10. The mobile response unit of claim 1, wherein storing the one or more medical records includes storing the one or more medical records in the memory and an external database.

11. A resident displacement manager for managing transfers between a displacing facility and a receiving facility, the resident displacement manager comprising:
a processing circuit including a processor and memory, the memory having instructions stored thereon that, when executed by the processor, cause the processing circuit to:
receive, from one or more receiving facilities, an indication of a number of available beds;
determine, based on the indication, a number of available beds within a threshold distance of the displacing facility;
display, to the displacing facility, the number of available beds within the threshold distance of the displacing facility and a distance associated with at least one of the available beds;
receive, from the receiving facility, an indication of a transfer of (i) a resident to one of the available beds and (ii) a caretaker associated with the resident from the displacing facility, wherein the caretaker includes a healthcare professional; and
electronically send one or more records associated with the resident to the receiving facility.

12. The resident displacement manager of claim 11, wherein displaying the number of available beds includes displaying an indication of a receiving facility of the one or more receiving facilities associated with each of the available beds.

13. The resident displacement manager of claim 11, wherein displaying the number of available beds includes displaying characteristics associated with each of the available beds.

14. The resident displacement manager of claim 11, wherein the resident displacement manager facilitates editing of the one or more records and creation of new records.

15. A method of managing a patient population for a disaster, the method comprising:
soliciting, from one or more receiving facilities, an indication of a number of unoccupied beds associated with each of the one or more receiving facilities;
generating, for a displacing facility, an interface including an indication of each of the unoccupied beds associated with the one or more receiving facilities, wherein the interface includes a distance associated with at least one of the unoccupied beds;
retrieving, from an external database based on a selection of the unoccupied beds, one or more records associated with a patient; and
transmitting, to a receiving facility of the one or more receiving facilities associated with the selection, the one or more records and an indication of a transfer of (i) the patient and (ii) a caretaker associated with the patient from the displacing facility to the receiving facility, wherein the caretaker includes a healthcare professional.

16. The method of claim 15, wherein the interface includes an indication of a distance associated with each of the unoccupied beds.

17. The method of claim 15, wherein the interface is displayed to a user at the displacing facility on a mobile response unit.

18. The method of claim 17, wherein the mobile response unit is configured to communicate using a high-bandwidth bonded failover connection.

19. The method of claim 18, wherein the high-bandwidth bonded failover connection combines two or more cellular network connections.

* * * * *